United States Patent
Blum et al.

(10) Patent No.: US 12,054,763 B2
(45) Date of Patent: *Aug. 6, 2024

(54) METHODS FOR ORGANIC ACID PRODUCTION

(71) Applicant: S&P Ingredient Development, LLC, Saint Louis Park, MN (US)

(72) Inventors: Paul Blum, Monterey, CA (US); Sambasiva Rao Chigurupati, Omaha, NE (US); Derrick Jermaine White, Lincoln, NE (US)

(73) Assignee: S&P Ingredient Development, LLC, Saint Louis Park, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/188,061

(22) Filed: Mar. 22, 2023

(65) Prior Publication Data

US 2023/0265467 A1    Aug. 24, 2023

Related U.S. Application Data

(60) Division of application No. 17/073,977, filed on Oct. 19, 2020, now Pat. No. 11,613,769, which is a continuation of application No. 16/443,554, filed on Jun. 17, 2019, now Pat. No. 10,808,266.

(60) Provisional application No. 62/686,463, filed on Jun. 18, 2018.

(51) Int. Cl.
| | |
|---|---|
| *C12P 7/52* | (2006.01) |
| *C12N 1/20* | (2006.01) |
| *C12R 1/02* | (2006.01) |
| *C12R 1/145* | (2006.01) |
| *C12R 1/225* | (2006.01) |

(52) U.S. Cl.
CPC ............... *C12P 7/52* (2013.01); *C12N 1/205* (2021.05); *C12R 2001/02* (2021.05); *C12R 2001/145* (2021.05); *C12R 2001/225* (2021.05)

(58) Field of Classification Search
None
See application file for complete search history.

(56) References Cited

U.S. PATENT DOCUMENTS

| | | | |
|---|---|---|---|
| 1,932,755 | A | 10/1933 | Stiles et al. |
| 10,808,266 | B2 * | 10/2020 | Blum .................... C12N 9/485 |
| 2004/0033289 | A1 | 2/2004 | Selmer-Olsen |
| 2011/0151529 | A1 | 6/2011 | Yang |
| 2015/0275242 | A1 | 10/2015 | Osterhout et al. |
| 2017/0145467 | A1 | 5/2017 | Svagelj et al. |
| 2019/0382809 | A1 | 12/2019 | Blum |
| 2021/0040513 | A1 | 2/2021 | Blum |
| 2023/0097164 | A1 | 3/2023 | White et al. |

FOREIGN PATENT DOCUMENTS

| | | |
|---|---|---|
| CN | 101967498 | 2/2011 |
| CN | 102076863 | 5/2011 |
| CN | 102686718 | 9/2012 |
| CN | 106868062 | 6/2017 |
| CN | 107937314 | 4/2018 |
| CN | 113614221 | 11/2021 |
| EP | 0141642 | 5/1985 |
| EP | 2648530 | 10/2013 |
| FR | 2686897 | 8/1993 |
| JP | 2008259451 | 10/2008 |
| JP | 2011524749 | 10/2017 |
| WO | WO 198504901 | 11/1985 |
| WO | WO 2010097362 | 9/2010 |
| WO | WO 2012064883 | 5/2012 |
| WO | WO 2014099707 | 6/2014 |
| WO | WO 2017055932 | 4/2017 |
| WO | WO 2017185018 | 10/2017 |
| WO | WO 2019245985 | 12/2019 |

OTHER PUBLICATIONS

Abdel-Rahman et al., "Recent Advances in Lactic Acid Production by Microbial Fermentation Processes," Biotechnology Advances, Nov. 2013, 31(6):877-902.
Accession No. A0A0F3WHB9, Jun. 24, 2015, 5 pages.
Accession No. Q6AA87, Sep. 13, 2004, 2 pages.
Ahmadi et al., "An overview of biotechnological production of propionic acid: From upstream to downstream processes," Electronic Journal of Biotechnology, 2017, 28:67-75.
Border et al., "Production of Propionic Acid by Mixed Bacterial Fermentation," Biotechnology Letters, 1987, 9(12):843-848.
Coral, "Propionic acid production by *Propionibacterium* sp. using low-cost carbon sources in submerged fermentation," Dissertation, Federal University of Parana, 2008, 39 pages.
Duarte et al., "Microbial production of Propionic and Succinic acid from Sorbitol using Propionibacterium acidipropionici," AMB Express, 2015, 5(13):1-8.
Eitman and Ramalingam, "Microbial Production of Lactic Acid," Biotechnol. Lett., May 2015, 37(5): 955-75.
European Extended Search Report in EP Appln. No. 19823109.4, dated Feb. 14, 2022, 16 pages.
European Extended Search Report in EP Appln. No. 21753482, dated Jul. 18, 2023, 8 pages.
Gonzalez-Garcia et al., "Microbial Propionic Acid Production," Fermentation, 2017, 3:21, 20 pages.
Guan et al., "Comparative Genomics and Transcriptomics Analysis-Guided Metabolic Engineering of Propionibacterium acidipropionici for Improved Propionic Acid Production", Biotechnology and Bioengineering, Dec. 2017, 115(2):483-494.
Guan et al., "Metabolic engineering of acid resistance elements to improve acid resistance and propionic acid production of Propionibacterium jensenii," Biotechnology and Bioengineering, 2016, 113:1294-304.

(Continued)

*Primary Examiner* — Christian L Fronda
(74) *Attorney, Agent, or Firm* — Fish & Richardson P.C.

(57) ABSTRACT

Microbial cell lines suitable for industrial-scale production of organic acids and methods of making and isolating such cell lines.

19 Claims, 2 Drawing Sheets
Specification includes a Sequence Listing.

(56) References Cited

OTHER PUBLICATIONS

Guan et al., "Understanding of how Propionibacterium acidipropionici respond to propionic acid stress at the level of proteomics," Scientific Reports, 2014, 4:6951.

Guan et al.,"Genome-shuffling improves acid tolerance of Propionibacterium acidipropionici and propionic acid production," Advances in Chemistry Research, 2012, 15:143-152.

International Preliminary Report on Patentability in International Appln. No. PCT/US2019/037520, dated Dec. 22, 2020, 10 pages.

International Preliminary Report on Patentability, International Application No. PCT/US2021/017940, dated Aug. 25, 2022, 7 pages.

International Search Report and Written Opinion in International Application No. PCT/US2019/37520, dated Oct. 29, 2019, 17 pages.

International Search Report and Written Opinion in International Application No. PCT/US2021/017940, dated May 3, 2021, 9 pages.

Invitation to Pay Additional Fees in International Application No. PCT/US2019/37520, dated Aug. 30, 2019, 2 pages.

Jiang et al., "Enhanced propionic acid production from whey lactose with immobilized Propionibacterium acidipropionici and the role of trehalose synthesis in acid tolerance," Green Chem., 2015, 17:250-259.

Kagliwal et al., "Wheat flour based propionic acid fermentation: An economic approach, " Bioresource Technology, 2013, 139:694-699.

Kizer et al., "Application of Functional Genomics to Pathway Optimization for Increased Isoprenoid Production," Applied and Environmental Microbiology, May 2008, 74(10):3229-3241.

Liu et al., "Glycerol/Glucose Co-Fermentation: One More Proficient Process to Produce Propionic Acid by Propionibacterium acidipropionici," Curr Microbiol., 2011, 62:152-158.

Luna-Flores et al., "Improved production of propionic acid using genome shuffling," Biotechnology Journal, 2017, 12(2):1600120, 1-12.

Parizzi et al., "The genome sequence of Propionibacterium acidipropionici provides insights into its biotechnological and industrial potential", BMC Genomics, Oct. 2012, 13(562): 1-20.

Prather et al., "De novo biosynthetic pathways: rational design of microbial chemical factories," Current Opinion in Biotechnology, Oct. 2008, 19(5):468-474.

Rehberger et al., "Response of cultures of Propionibacterium to acid and low pH: tolerance and inhibition," Journal of Food Production, 1998, 61:211-216.

Scholz et al., "The natural history of cutaneous Propionibacteria, and reclassification of selected species within the genus *Propionibacterium* to the proposed novel genera *Acidipropionibacterium* gen. nov., *Cutibacterium* gen. nov. and *Pseudopropionibacterium* gen. nov.," International Journal of Systematic and Evolutionary Microbiology, 2016, 66:4422-4432.

Stowers et al., "Development of an industrializable fermentation process for propionic acid production," J Ind. Microbiol. Biotechnol., 2014, 41:837-852.

Suwannakham et al., "Construction and characterization of ack knock-out mutants of Propionibacterium acidipropionici for enhanced propionic acid fermentation," Biotechnology and Bioengineering, 2006, 94:383-95.

Suwannakham et al., "Enhanced propionic acid fermentation by Propionibacterium acidipropionici mutant obtained by adaptation in a fibrous-bed bioreactor," Biotechnology and Bioengineering, 2005, 91:325-337.

Suwannakham, "Metabolic engineering for enhanced propionic acid fermentation by Propionibacterium acidipropionici, " Dissertation, Ohio State University, 2005, 278 pages.

Taniguchi et al., "Production of a Mixture of Antimicrobial Organic Acids from Lactose by Co-Culture of Bifidobacterium longum and Propionibacterium freudenreichii," Biosci. Biotechnol. Biochem., Jan. 1998, 62(8):1522-1527.

Thierry et al., "New insights into physiology and metabolism of Propionibacterium freudenreichii, " International Journal of Food Microbiology, 2011, 149:19-27.

Tufvesson et al., "Economic and environmental assessment of propionic acid production by fermentation using different renewable raw materials," Bioresource Technology, 2013, 149:556-564.

Wang et al., "Engineering *Propionibacterium freudenreichii* subsp. *shermanii* for enhanced propionic acid fermentation: Effect sof overexpressing propionyl-CoA:Succinate CoA transferase," Metabolic Engineering, 2015, 27:46-56.

Wang et al., "High Cell Density Propionic Acid Fermentation with an Acid Tolerant Strain of Propionibacterium acidipropionici," Biotechnology and Bioengineering, Mar. 2015, 112(3):502-511.

Wang et al., "Metabolic engineering of *Propionibacterium freudenreichii* subsp. *shermanii* for enhanced propionic acid fermentation: Effects of overexpressing three biotin-dependent carboxylases, " Process Biochemistry, 2015, 50:194-204.

Wang et al., "Propionic acid production in glycerol/glucose co-fermentation by *Propionibacterium freudenreichii* subsp. *shermanii*," Biosource Technology, 2013, 137:116-123.

White, "Wheat Flour Hydrolysis Protocol," dated Mar. 5, 2018, 1 page.

Woskow et al., "Propionic acid production by a propionic acid-tolerant strain of Propionibacterium acidipropionici in batch and semicontinuous fermentation," Applied and Environmental Microbiology, 1991, 57(10):2821-2828.

Zhang et al., "Effects of carbon dioxide on cell growth and propionic acid production from glycerol and glucose by Propionibacterium acidipropionici," Bioresource Technology, 2015, 175:374-381.

Zhang et al., "Propionic acid production from glycerol by metabolically engineered Propionibacterium acidipropionici," Process Biochemistry, 2009, 44:1346-1351.

Zhu et al., "Optimization and scale-up of propionic acid production by propionic acid-tolerant Propionibacterium acidipropionici with glycerol as the carbon source," Bioresource Technology, 2010, 101:8902-8906.

Zhuge et al., "Improved propionic acid production from glycerol with metabolically engineered Propionibacterium jensenii by integrating fed-batch culture with a pH- shift control strategy," Bioresource Technology, Jan. 2014, 152:519-525.

Zhuge et al., "Improved propionic acid production with metabolically engineered Propionibacterium jensenii by an oxidoreduction potential-shift control strategy," Bioresource Technology, Jan. 2015, 175:606-612.

\* cited by examiner

SEQUENCE LISTING

```
Sequence total quantity: 29
SEQ ID NO: 1            moltype = AA  length = 258
FEATURE                 Location/Qualifiers
source                  1..258
                        mol_type = protein
                        organism = Propionibacterium acidipropionici
SEQUENCE: 1
```

```
MSDGGISPGD RLARAHSFGE AAADYQRYRP DYPIEAVTYL VAGTPAGGRV LDLGAGTGKL    60
TDRLVALGFE VVAVDPSAQM LAELSRRRPD VDCRVGTGES LPLPDSCVDG VVCGQAWHWM   120
DAGAVGRELA RVMRPNGSLG LAWNTDHTDT GWLARIEAIR NVPRGAELNR GPDRTPVSPG   180
QGWSPFTRHD VDWTRTMTKE DFLALWRTHS QWLTATEEQR IRWMSGWRDV LATDPQVATL   240
DTVSIPMTTE CWVTRPGG                                                258

SEQ ID NO: 2            moltype = AA  length = 412
FEATURE                 Location/Qualifiers
source                  1..412
                        mol_type = protein
                        organism = Propionibacterium acidipropionici
SEQUENCE: 2
MLGDATGRLR VGEQKQAGRG LSRGLLLLMA TATGLAVGGN YLNQPLIDEI ARHFSVSVST    60
AATSVTVTQF AYALGLVLFV PLGDMINRRK LAVTLFLVSA AGLLTAAVSG SFAVMMIGTA   120
IASLFSVAAQ VLVPFASELA APGRGGAAVG TMMTGLLTGI LVARAVSGML SLVGGWKTAY   180
WVLGVLLLVM AATLWKMLPD VPVAESFSLT RVPASMGRAW MRYPKVRSRA VISALLFASV   240
SACFATMTPL LAGPPHRLGP GVIGILGLLG LVGAFAAGPV GRMADRGLGN RTVVLGLVIL   300
AAGWASMWFA TGSVVMFGIG FILTDLGLQS AHVTNMNVVY AQEPALRSRL NSLYMTMYFI   360
GGSVGSAVAV GLWSRFAWHG VVIAALAFVT AAGVVFALER LSDRRPRIAS QG           412

SEQ ID NO: 3            moltype = AA  length = 264
FEATURE                 Location/Qualifiers
source                  1..264
                        mol_type = protein
                        organism = Propionibacterium acidipropionici
SEQUENCE: 3
MALLIILIIL VVVIGGGVGL FIAPYNSFVK LRNTIQESWR QVDVELNRRY ELIPNLVETV    60
RAGAAHERNT LEEVTRLRNQ AVAMATNSQG NTPDPQRSQI ESQLSGAVHN LVAQVEAYPE   120
LRSNTNFLEL QRELSDTEDR IAAGRRYYNA NVKTYNTKVE SFPSNLVAGM FHFEKASYFQ   180
VDDPAVRSAP GVNFGEISQR PEAQQNQGQA PQIGQGNPAQ APGYAAPQAS GQLPDPQAAR   240
QPDPSQQPWG TQGKPGDQGN QNSQ                                         264

SEQ ID NO: 4            moltype = AA  length = 166
FEATURE                 Location/Qualifiers
source                  1..166
                        mol_type = protein
                        organism = Propionibacterium acidipropionici
SEQUENCE: 4
MSANPVPQVP GTGTLLADVF RWHPAGVAVL TADGPSRPVG ITVSSLASVS VAPPMVSVSM    60
ANSSTTLAAL HLGGRAVVHL LDAGQEDLAD SFARPGVPAV GIDWERTAEN APQLDVETPR   120
LHAVVARMID TGSATLVALT IERIEVGRRG SAALVRMGRG WYTLPR                  166

SEQ ID NO: 5            moltype = AA  length = 210
FEATURE                 Location/Qualifiers
source                  1..210
                        mol_type = protein
                        organism = Propionibacterium acidipropionici
SEQUENCE: 5
MSEQTSPASP TPGPRPVTEI GTLPPIDVVE KRLPVDPATG RPRREILATI ATICYILAAG    60
ASAVALARAW WGTINMRTFH LATNLMTWTD PRPGSLASVL LAALMMVIGG VMVAMPALLA   120
VNTWLGRRWV RWGAIGGVAA AVLAVTLNPL AWISAPFSIA GGVMVWLPST RRWFELWRQV   180
RSEPEVERFT PRPITYGPVA KHMWPPGRRT                                    210

SEQ ID NO: 6            moltype = AA  length = 390
FEATURE                 Location/Qualifiers
source                  1..390
                        mol_type = protein
                        organism = Propionibacterium acidipropionici
SEQUENCE: 6
MSQGEPGYRR ASLALLAAGL ASFNALYCTQ ALMPTLTSQL GATPAQASLT VSAATGILAI    60
TILPVSVLSE RFGRGRLMTI SAMAAVVVGL LLPLAPSLGW LVVGRGLQGL LVAGVPATAM   120
AWLSQEIHPR HLPRAMGLYV AGNTVGGLLG RLIPSGVLQF TGWRPALGID MAFALVCTVA   180
MVTLMPAERR FVPKQLRPGN ELRTMGRQWA DRRLAGLFGI GFIFMGVFVS LYDFLGYRLT   240
ARFGMPPSLI GLVFLLYLFG TLASARAGHL TATRGRGPAM LIGAAMAIVG MPLVASGLLW   300
LTLPGVALFT YGFFTVHSVA SGWVGALAPR ARGEASGTYL ACYYLGSSIL GYLSGHVMHA   360
FGWTGLVMWL VGLILIGCAL SAMVVRSARS                                    390

SEQ ID NO: 7            moltype = AA  length = 391
FEATURE                 Location/Qualifiers
source                  1..391
                        mol_type = protein
                        organism = Propionibacterium acidipropionici
SEQUENCE: 7
MAATATRPPR DRRPSVVHLS TVHNRHDNRV FNKEARALVN AGYDFHLVIS ADADGVDDGI    60
PVVGLHRTVG PRLRRIVAGQ LEAWRVLGSL RPELLQIHDP ELIPMALLWG RTHPCKVVYD   120
AHEDLVGQID TKPYLNRLTR PVARAAARCL VGMADRGADG IVAATEPVAD RFRNPRIAVV   180
HNYPWLANFT VDPAPVPGRL VYAGDLSQER KLSFMIDVVR ALRATVPAAH LVLAGRALKG   240
CGPVVEAGVA EGLVDYRGLV GPTEVPGVLA SAQVGLVFLE PLPNYVRSLP TKLFEYMAAG   300
VPFCASDFPA WSQMFSGYGA GAFADSESVE TTANVLAGLL TDPQGCEQMG EAGRRAIGEG   360
```

```
LTFEAQSRAL LTLTEELLGC GAGPLGGGER Q                                         391

SEQ ID NO: 8           moltype = AA  length = 451
FEATURE                Location/Qualifiers
source                 1..451
                       mol_type = protein
                       organism = Propionibacterium acidipropionici
SEQUENCE: 8
MGACAEALLW LLFIVLTFIS TDQAIASDRA YPMLLVVLGV AGAGCLVLGV LRRREGRSAV  60
SGSGIGRPGW RALGLTALPF LAMLCWAGIT IPFATHVALS NRFGPLVHIR LPMASMVVPL  120
VEAALVVLVA VGLVVGIGRR RLPEALWRAF LVLAASTLIS IVWQVATRHA MVRRAVDGKL  180
MWRTSTQLGG QATYHLALLL GIGVAVDAIR RRYRVGVSWL IIAGLGLAIV LSGSRAGLIC  240
LGLFCVALFI WGRPAGGRGG GGRRRTLVGV LGLAALAVVA GALLWLRGGA LVDHDRAQTW  300
KVAWRAVTAD PTTVIVGRGY ATIWPWFATE TGIVPGAIHG LRPGPFGKSL VHAHNTVVQV  360
GGELGIIGLV LLLVSVVGVA VLAFRGIHGR HLGICLALLA SLPALVLDTY LVKNFQVSLV  420
WWLVAAAVAV LMARPADHDQ PTNSDQPADR P                                451

SEQ ID NO: 9           moltype = AA  length = 455
FEATURE                Location/Qualifiers
source                 1..455
                       mol_type = protein
                       organism = Propionibacterium acidipropionici
SEQUENCE: 9
MSRRAFRYRD TTPGTVLGVV AAMLVLRLPL SFLLFVVAPW FLILTGAIAK GGSVRCLPLK  60
AMLGWCLVAA TISIAVLHPG VAASTGNNVV IMIAVIGCTL VVHRGQAPGL TARRTLAGLY  120
WGAGGVWLIA MGEMITGIKL LPILYPDANT VSYVQSSRFI VSATYPNIND FSVVLVMLVT  180
AVVARMWFDR ARGWRNAGRW LVLLTSLFMV VMSTSRGALV GCLAGVALLI VLNVRRLHPH  240
ALGVRAGLFG GGLIVPVGAV FFTSSYVQDH STATRGQIFN NAMSMLAGSP ADALLGYGSL  300
ASYQSAAKAA FGDVLMDPHN MLLEITLNYG VIALVLFIVV WLWVLMRGFL PRRPMADWQT  360
AFGLTTVVLL PLLGVVPSST LRYHVTWIYL AATTLLVAEG AEARTPTRPE LSDEQPSGRE  420
LSGSDTSGAT AADGDLGHAH DDHARDQAEH HSDHR                            455

SEQ ID NO: 10          moltype = AA  length = 437
FEATURE                Location/Qualifiers
source                 1..437
                       mol_type = protein
                       organism = Propionibacterium acidipropionici
SEQUENCE: 10
MARRHGLIGG WREPMGRQRV WLPVAGLSAL LVVETFFDLR RSMTPSPWLW NSYLIVHLLA  60
ALACLVLILA GRDGNRFSRA GWIVIGFAAA LMACSLVSAA VTPLPRVSYV TVPRAYLVVP  120
TLTAAATLLL GAAVVRVLPD QPVHRVLWWP AALTLACAFA QWPRSAVVHG SPRLATGMGG  180
SAVVHVPLLL ATGVALAAFL AGWRRWWSLG LTVIGVAAVV LTGSRSGVVC LVLAGVVVGL  240
QWLRSRRAWL VAGAAVVALG IVVAAVPMLH RLLNPTDELR AKNLETALGV WTETPKHLLL  300
GVGSGRLWPW YAFDSHLLRT PWRGMVTTEW GPALNSAHST FLQVLVELGL LGMLLLIPVV  360
VVPVVVLARR LWPGLRGAAR PVPDTVPLIA LVATVPAFFL DTYLLKNYGA SLWWWLVVLR  420
CLRRAQSAPS TSVQNRG                                                437

SEQ ID NO: 11          moltype = AA  length = 767
FEATURE                Location/Qualifiers
source                 1..767
                       mol_type = protein
                       organism = Propionibacterium acidipropionici
SEQUENCE: 11
MAEPRHAGRR GARHGKAKRR KGSPFGRFVK RTLFSLLILV LVLAIAAGVG AIVFYNRTNL  60
PDPNKDFQTN TSFIYFNDSK TKLGSLSVQN RQTISYEQMP KSIKDAAISA ENRTFWEDQG  120
ISIGGIVRAA WTIARGGEMQ GGSTITQQYI KILYLSQDRT MQRKLKELVL AVKMGKQVPK  180
EDILAGYLNT IYFGRGAYGI QAAAKSYFNV DASKLTVPQS AVLASILNNP TLFDASGGTK  240
ARERRLLNRYR YVLDGMLEAG NITQAQHDEY SRKLPAFPEV PINNRWGGTN GYLLKMVQNE  300
LLDDGFTDSQ INGGGLKVTT TFDPAAQKAA VATGQKYKKL AGSNAGKNGA KNLHPAIASV  360
KVGTGEVLAL YGGDDYITST RSWALQARPA ASTFKTYAVI AGMRNGFSLK SKLNGDTFTP  420
QGDSVPIRNE FSEQYGDVTL QKATEDSINT AFVDMMTQID NGPQAMLKAA NDAGVPKGSG  480
WDLNNRMPLG VAEVSPLDQA TGYATIANEG KYVPSHVVAK VTDSSGKTLY TAKTTGKQTI  540
QKDIAHDTTY ALENVVNEGT GSAVSNLGYP VAGKTGTNGV KDDITSAWFV AYTRQISTAV  600
MYVAGDSGNA DLDPYAAPGD ATFFGGTYPA RTWADYMKVA MKGLPAKDFP DPDWVNLSGN  660
HYGDTQRETL RTPTPTPTPT QAPTTATSQP TVTATATQPT QQPTTQPPAT VQPTQEPTTS  720
TATNRPTSTA TNGSGGDGDG GGGDGGDGGG GNGNNGNGAN AAPGGNG                767

SEQ ID NO: 12          moltype = AA  length = 297
FEATURE                Location/Qualifiers
source                 1..297
                       mol_type = protein
                       organism = Propionibacterium acidipropionici
SEQUENCE: 12
MVSSTPPAEV DITVDLVHAL LAEQHPDLAD RRLKVVANGW DNVIVRIGED LVARLPRRQL  60
AADLILHEQR WLPELARGLP ILVPAPVRQG RPGHGYPWFW SICPWFEGEV AADVPLADPV  120
READRLGAFV HAFHRPAPPD APSNPFRDIP VARLAPRTRG NLEQLGPGHE SVAALIDRLA  180
AVPAWDSPPV WVHGDLHAAN LLVADGRICA VLDFGDLTAG DPAVDLAVAW MLFDADDRRR  240
FRIAAGGGAP VDDATWDRAR LWGLHLGLIF LLHSEDSEQF SRLGARLFRA VTSEDAG     297
```

```
SEQ ID NO: 13              moltype = AA   length = 260
FEATURE                    Location/Qualifiers
source                     1..260
                           mol_type = protein
                           organism = Propionibacterium acidipropionici
SEQUENCE: 13
MTRTMTLPDG RTMAWEEYGA ADGRPVLFLH GTPGGRLSAA KYEPFALARG LRLVAPDRPG    60
YGLSTARPGM TLSDYAEALL DLCWWRGWGP VPVVAGSAGA AYALALGAAA SEMVTGVSIF   120
SGIAPMTDDE ARTLIPVNQQ LRCAVDDPAE LQRLVGQVRD AILAGTLKGL PEDPALTDAL   180
KPGADGMVAD YRNVFGEWGP DPVAVRVPVL WIHGTDDVNA PISAARRLAS QLPEARFEEV   240
SGGVHAPSAE TLERVFDATP                                               260

SEQ ID NO: 14              moltype = AA   length = 249
FEATURE                    Location/Qualifiers
source                     1..249
                           mol_type = protein
                           organism = Propionibacterium acidipropionici
SEQUENCE: 14
MQYTLIDGLQ KLLSKALSVL AAWLLVRIID HGGFRDLALS VGWSRGLMGS LIALIVGLVV    60
SGIAILAGDG IGLLSNTGFG ESFHEQSVTL LILSIVLSIV FAAIYAVGMN TLWFGYLLRS   120
LSGRPVIGVV VVSLVPALVS LLPAPTSRFD PSILALMAQS TPEAVGVGLA SAVMVLALRS   180
VWPSVGIAVG ARLISLVSPG AMTSPSAATA VSQSAITGAL FAVAALVTAL LMGRHRWQQV   240
AHVGPFATT                                                           249

SEQ ID NO: 15              moltype = AA   length = 396
FEATURE                    Location/Qualifiers
source                     1..396
                           mol_type = protein
                           organism = Propionibacterium acidipropionici
SEQUENCE: 15
MEPMGVGVIG TGDISDVYLA NLNKYPGFVR LVACQNRTRA KAERQAARYG IGRVHDTVEE    60
LLADPEVKLV LNLTTPEAHA PINMAALSAG RHVYSEKPLA TSLEDARRTL DHAHDLGLHL   120
GCAPDTWLGG RAQTMRDLID SGEIGEVTAG VATIVYPGLE WFHPSPFQSY RADVGPLADI   180
GIYYVSMLVA LLGPVRQVAA MGKKTFDERT AHYGPIAGRP IPVEVETHVS ASLEFEQGAV   240
VTLLVSTDVP DSQLPRMELY GTRGTLCMPE TEPMAGPNTF GGPLWIRTLD DARYKDIPRP   300
APTPWTEAEN RHRFNETDFG ADPSVPRINS RGIGLVDEVL AIAEGRPMRC SGDLACHVLD   360
VIESIYASSR QRRFVEVASS CRRPAPLPAD FPGPQV                             396

SEQ ID NO: 16              moltype = AA   length = 311
FEATURE                    Location/Qualifiers
source                     1..311
                           mol_type = protein
                           organism = Propionibacterium acidipropionici
SEQUENCE: 16
MALNEVTFPS HDGRDQIHGW IYSPVRPVRG IVQIAHGLGE HSRRYLHMIT TLLDAGFVVA    60
ADDHAGHGAT AMASGVWQDT GPHGVDTVLI DERTLHDLAV ELHPDLPFVF FGHSWGSMIA   120
RGYASRYPDD LSALVLCGIA AGMHGIEETL DRDALAAAIA EGDGSGPDTG FQDQMFDGFT   180
SRCGPDAGPT AWVAADPQVV ADHGIDPLNN FGAPMSLRFV RDFARLYDEV NDAAWPGTVP   240
ATVPVLILAG EQDPVANYGE GALTVANQLW DTGHEVETRI YTGVRHEVHN EPATRAQVEA   300
DLLAFVERVT G                                                        311

SEQ ID NO: 17              moltype = AA   length = 488
FEATURE                    Location/Qualifiers
source                     1..488
                           mol_type = protein
                           organism = Propionibacterium acidipropionici
SEQUENCE: 17
MSSPSKTSAS PQATQGGSAP APQMKGRHLV MMSLGSAIGT GLFLGSGKGI AAAGPSVLVA    60
YVVAGLVVIA IMRMLGEMVA AHPDSGAFSV YTARAMGPAA GFAMGWVWWV ELAVVVAAEG   120
TAAAQIFLAV WPIAPDWLLT LIFMVALTAI NLFGVDKFGE FEFWFALIKV AAVVAFLVIG   180
VLLLCGVFPA PAPGLSNFLH HGGFMPNGWG GVATGLLIVI FAFGGIEIVA VAAAETENPR   240
KHVGKAINTI IWRILVFYMG SVAIMVFALP WDDPKLASSP FVAVLDLAKI PGADAVLTLI   300
IVLAVLSSLN ANLYGDSRML GSLAERGLAP KAMTGKNRRN VPVAAVLSSV APGYVCVVLT   360
YIWGAKVLDV LLNVVGSVII VTYLFTIASQ IILRRRAEKT GEELPFRMWG YPYLSWLTLA   420
VLIGIIGLGM TDAGVRGQIL ATFGLTVVLF VIGIVRTRRL GQDPFKPVVT PGDRLVDADP   480
AAEPAGTD                                                            488

SEQ ID NO: 18              moltype = AA   length = 520
FEATURE                    Location/Qualifiers
source                     1..520
                           mol_type = protein
                           organism = Propionibacterium acidipropionici
SEQUENCE: 18
MAPRPTSTDA PDDSAASDEE EVVELGTGRR ITEPLRAPTA GIPAHAPRVV EMGAETVPLR    60
APGVAALVEE LGLTASMTHP RPGPALLSSR RGAVPMPDGV TPTGPTRLLP TVRSQILSPS   120
GLLRAAAEPI TGRRHIDGDV SVGEFIETRF GPQVARAVVD PLLGAIHAAD INRFSLAAAA   180
PALVETAAEG DSMLLGTLGR EARRAAGWAR GLPLRGYHRM IRMMGLQEED LDRQAPAPSL   240
ASWPRGTATL ADRLAASVRA RGTLLLNTRA TRLTPPNDGG TAWRVGVEGL DGARELTADA   300
VVVATGSASA AGMLADVSPR AAEILAGLRA VSVATVILDL PLDETLAAHP LSGAATWFIG   360
```

```
SGWSPLIRQV  TNLSHKWPTT  LGGDRLVLRV  SAGRDGGRPL  DAMTDDDLAR  AVVAELRRLG   420
LPVAAPAEAV  TVPSKDARRR  MCTLVARFPN  AMPQPAPGHR  GRMESLAAAL  SEVPGLGLGG   480
CATDGAGVGT  AILAGRRLAR  QISAFLDRDP  RDPREQGGTL                          520

SEQ ID NO: 19           moltype = AA  length = 256
FEATURE                 Location/Qualifiers
source                  1..256
                        mol_type = protein
                        organism = Propionibacterium acidipropionici
SEQUENCE: 19
MLVSEVMSQQ  TPMSRVVGPW  TEWMGRWPTP  DDLAEEEAGA  AVAAWGRLGY  PRRALRLHAA    60
AVAIAERFDG  VVPSTYAELI  ELPGIGDYTA  AAVVSFAFGG  RAAVLDTNVR  RVLARVETGV   120
ANCGSATSRA  DRDLAAKWLP  ESDDDAARWA  VSSMELGALV  CVARAPLCES  CPVAGHCRWL   180
EAGKPTDGAP  VRRGQAWKGT  DRQCRGVILD  LVRNSAGGVE  VEVALEAWPK  RHQAEKCLGT   240
LLDDGLIHRE  GSVLRL                                                      256

SEQ ID NO: 20           moltype = AA  length = 627
FEATURE                 Location/Qualifiers
source                  1..627
                        mol_type = protein
                        organism = Propionibacterium acidipropionici
SEQUENCE: 20
MTVVLIIVIA  ALFIVAAAEL  LADRTGIAAP  ILLLLLGAGV  ALIPGMPEVE  VEPELVLMII    60
LPPLLYSSAV  NMPVADFRRN  LAPISVLAVA  LVAVSAAVIG  FIVNQMVPGI  GIAACVALGA   120
IVSPTDAVAT  SIVKKAGVSR  RLVTVLDGEG  LINDASALVI  LSSAVGAMFA  EISAGEVILD   180
FVLAVVVAVV  VGWLVGHAMI  WIRARIHEAT  PDTVLSMATP  FLAFLPAEHL  HGSGLVAAVA   240
AGLVASHQGP  RVLTPTQRMS  SRTTWRSLML  ILESAVFLLM  GLELTAVVED  MEAESFGWKL   300
AVAVAAVALV  MTMVLRTVVV  TPLLMWVTRR  SKRRSKHRSY  LEKASQKVAD  ALESDEEITI   360
RGNTIDADHA  ARFRHRIVRT  ISDLDYYIKH  PLGPREGSVM  IWAGMRGAIT  LAAAQTLPLD   420
TPHRSFLVFV  AFLVAAASLL  IQGSTLGLVV  KVAKPATSEG  VDPDEQAEIR  KLMHRAARKV   480
PVPAPMRRLL  ARTGHQESED  VEENRAQAAA  VALAWRQFAA  LRDRGVESEA  PAEAGPERLG   540
ETAPIPRIVG  KQLPGEDARA  KVLASPEHRR  RAAEISRQYA  LRLIVAQRKV  LLDANDAGRF   600
SPEAVSSALD  TLDADQLSLE  ARGTSLD                                         627

SEQ ID NO: 21           moltype =   length =
SEQUENCE: 21
000

SEQ ID NO: 22           moltype = AA  length = 540
FEATURE                 Location/Qualifiers
source                  1..540
                        mol_type = protein
                        organism = Propionibacterium acidipropionici
SEQUENCE: 22
MSILRTKSVE  QSLRDTEDPE  HQLKKSLSWV  ELTMFGIGVV  IGAGIFTMTG  RVAHSMTGPS    60
IIIISFIVAAI  ACGLAAMCYA  EFASTVPVAG  SAYTFSYASM  GEIFAWIIGW  DLFLELFLAS  120
SVVAQGWSAY  LAVFLSQLGI  DLPPQIVSGG  RFDLLAFGLI  MVLGMLLIGG  IKESVRVNTV   180
LVAIKLFIVM  FVIFAGIGYV  KASNFTPFVP  DKQPVESTGG  LTQPLLQWFT  GSGQTAFGVS   240
GIVAGAALVF  FAYIGFDVVA  TTAEEAKNPK  RDVPLGILGS  LVVCTILYIA  ISLVLIGMVP   300
YDQLDPSASL  AKAFTTVGKP  WMAIIISAGA  VAGLTTVVLT  MMIGATRVIF  AMSRDGLLPE   360
GLSHVHPKTR  TPYRITLIIM  LADGLLAALV  PPGILDEMVN  IGTLLAFVMV  SVGIIVLRRK   420
RPDLPRAFRV  PWVPVVPIVS  AIICLYLMLN  LSIETWMRFL  IWMVIGIVVY  FTYSKNHSRL   480
AHGSELTADI  NAEITNVMGH  QYDARRGSRR  AGSPAAQASS  AGSAEPADAA  PELSDPPKES   540

SEQ ID NO: 23           moltype = AA  length = 674
FEATURE                 Location/Qualifiers
source                  1..674
                        mol_type = protein
                        organism = Propionibacterium acidipropionici
SEQUENCE: 23
MRDAMRATVP  ALALAVALSA  CSGSGQSRGS  ASASGDGVAS  LTETKVTPLV  SSIGSRDGAD    60
LKPVRLADGL  TPPTNRWFSG  MAYGSTAQPV  FPLPLSFSLL  GSGFALGLPD  IKTSDRTIMG   120
GNRPAVQIGA  GADSWKITRY  DEMSVTLTGS  AGGTEIGTVT  IARGSPFVTF  RASGRRTLTT   180
NLPFTGSGSP  WSLQAGEDRY  DLTGSKGVSV  SGGAVTVPDG  GHVTLYPEPE  GGDAAALARL   240
AASPLRSTAS  SYRLSGSTAT  TRLAYSTDDG  SPTAIAALPH  QQAGLATGQH  CDLGSYRSVL   300
GTMKLCRGTA  LSWDTKTRPA  TAQLDLSGLA  DDQRAALRTQ  VDADVRALKP  YPADTYFGGK   360
ALYRDAQLYT  LAKQVGASSS  ATTLKSRIVE  QLTKWADPSG  CGSRTSLCFY  YDRSNKGMVG   420
LTHSFGSEQF  NDHHPHYGYF  LYAAGVMAAD  DPSLVKRWKP  VMTLLAADIA  SPTDTGTFPQ   480
RRTFDPYSSH  SWASGVSPFG  DGNNQESASE  AVNAWVGLGV  WARAAGDPQL  AAEGTWMQAL   540
ESDSQLAYWT  NFDTDDPVYK  GFGHSITPLV  WGGKRDYATW  FSPEPAAALA  ILLIPMNPAS   600
GYLGTDPKRV  ATNLKEAMGT  RGYRQTYGDL  LLLYSALQGS  SQRDAAVKQV  ASLTSIDDSL   660
TRSYILAYLY  ALKF                                                        674

SEQ ID NO: 24           moltype = AA  length = 425
FEATURE                 Location/Qualifiers
source                  1..425
                        mol_type = protein
                        organism = Propionibacterium acidipropionici
SEQUENCE: 24
```

```
MTSPARAHVD DVISFVESSP TSYHAAAELA RRLEEAGFER LDETADWSGA ASVEGRRFVV    60
RDGAVIAWAT PETIGPRAGF RIVGSHTDSP SFKLKPHATF TNLGWQQVGM EVYGGGLLNS   120
WLDRDLGLAG RLVTLDGETH LVRTGPILRI SQLAPHLDRT VNQDLTLDRQ RHLMPILSVG   180
RPDLDVEDLL CEEAGIDRSR LGFHDILAYP TERPAVIGPA GEFLASSRMD NLSSVHSSIA   240
AMVDVEVGED IAVMACFDHE EVGSSTRSGA CGPFLEDVLV RIADGLGRRG DAYRAMIARS   300
TCISSDAGHG VHPNYPEKFD PANHPLLGQG PLLKINANQR YATDGVGGAL WQRVCRAADV   360
PTQAFVSNNS VPCGSTIGPL TATRLGMLTV DVGLPLMSMH STRELAGVAD LSSLSTALGA   420
FWAGA                                                              425

SEQ ID NO: 25           moltype = AA   length = 713
FEATURE                 Location/Qualifiers
source                  1..713
                        mol_type = protein
                        organism = Propionibacterium acidipropionici
SEQUENCE: 25
MPAPRTAFLD LSALAPAKTR PALIDADLAR FTAIAEAIDA QLTTLTAQRR DALSDTARTG    60
RAAAADRDQEV RRINSRIRIL RDVGPQICLG RMDRTGGEPV YIGRIGLSDD ADRRLLVDWR   120
TPAARPFFAA TVADPMGLAG RRRFRWRDGR VIDYWDEALI PDAGTDPATM DAESAFIASL   180
AASRSPRMLD VLATIRADQD AAVRAEARRP LIVEGGPGTG KTVVALHRAA YLLHADPTLN   240
NRGGGVLLIG PHPGYLAYTA DVLPDLGEDG ARTATVADLL PQGPDARPEP DTRVAALKLD   300
ARMAGAVEPA VALYEEPPTD TLTVDTPWGE VAVTAAAWTE AFSAAEPGSV HNEARDRIWH   360
DLIDILVDHA QSLDAPEDRL RRALYGDEEL REAFSRAWPI LNPEELVADL WEVPAYLRRC   420
APWLTPDEAA LLRRGPAHPW TTADLPLLDA ATRRLGDRRA GAAARRQAV LAEQRSYMDD   480
VVTHILDADD DPDSSLAMLR GADLRQVLLD TDALDDGTTD PLAGPFAHII VDEAQELADA   540
QWQMLIRRCP SLSFTIVGDR AQARDGFPES WEERLGRLGF HDMSRVTLSV NYRTPSEVME   600
AAEPVIHAAL PDAAVPTSVR SSGLPVRHGR IAHLDRIVAE WLDENPEGIA AVIGAPGFDG   660
GPRVRALSPA DVKGLEFDLV VIVDPEHFGD GITGAVDRYV AMTRTTSQLV ILR          713

SEQ ID NO: 26           moltype = AA   length = 436
FEATURE                 Location/Qualifiers
source                  1..436
                        mol_type = protein
                        organism = Propionibacterium acidipropionici
SEQUENCE: 26
MTHSENLTDI SRTIDDFDSI TDANKAVVDV MTAGQPVLVD VARAHTLIPE LDTGEKVLLH    60
AGPPIDFEHM PETIKGACIG AALFEGWASD EDAARRVVAE QVRLIPCHHV GAVGPMGGIT   120
SAHMALMKVV NTTYGNVSYS TLNEGIGKVL RFGGYDAEVI DRLGWMRDVL GPALSSALAT   180
TDGGYPLAPV MARALTMGDE MHQRNIAASA LFAKDMAPLL ARAGLPGDTV AEVSDFLGRT   240
DQFFLNVAMA ASKACADPAR QVRAGSVVTA MCRNGYEFGI RVSGLGDRWF TAPVNTPSGL   300
FFTGYDQSQA APDMGDSAIM ETFGLGGMSI VAAPGVTPFL GAGGFSEALA TTEEMAEVVT   360
AHNPNMPIPT WNFQGAPTGI DIRLVVQTGI TPIINSGIAS KHPGVGQIGA GTVRAPMGCF   420
TRAVEALAEV YGVDVS                                                  436

SEQ ID NO: 27           moltype = AA   length = 419
FEATURE                 Location/Qualifiers
source                  1..419
                        mol_type = protein
                        organism = Propionibacterium acidipropionici
SEQUENCE: 27
MVCPSTLFLV TNSYPLGTGE DFIENEIGDL AERFGRVVVV AVQTRPGDVI TRPVPGNVEV    60
IRAGGPRPAG RAALLAAARG LAHLPRGSWN RDTLRDPRRL GLEAMFEEHA RDTEADLLAQ   120
LPALGLRPGS HAVVYSYWFL DTARVAMLLA ADLRARGVVV DRLVSRAHGY DLYPERAPYG   180
HLPQRERLVA AFDAVCPVSE QGTRTLRSGW PGYAGKIGTH HLGTVGPGSP ADCSREPFHI   240
VSCAYLVPVK RMTRMPGVLA ELRGRGVDAR WTHLGGGPES EDVLKAARDA GVDEQVDLQG   300
HLAHEKILET ERGLRPSCLI NLSSSEGLPV SMMEEASLGI PLIGTDVGGV REIITDRVNG   360
RLINPDFTDS QAADTLQWLA DLPTDDYRSV CEASRRIWQS DYDQAVVYPR FCTEVLGAD    419

SEQ ID NO: 28           moltype = AA   length = 160
FEATURE                 Location/Qualifiers
source                  1..160
                        mol_type = protein
                        organism = Propionibacterium acidipropionici
SEQUENCE: 28
MRRYTITVAG TTHEIEVEET SATQFQVRVD GQQVEVELTA HQDVGDQPVV PQIDPRHESA    60
PKAPRVPQQV RTRATGSPSP ALTGGADLAY SMTAPMPGVI ASVDAGPGDE VAKGQTVLVL   120
EAMKMKNELH ASRSGVIAEV LVAEGDQVKY GQTLLCFEKA                        160

SEQ ID NO: 29           moltype = AA   length = 731
FEATURE                 Location/Qualifiers
source                  1..731
                        mol_type = protein
                        organism = Propionibacterium acidipropionici
SEQUENCE: 29
MGRFFKNLAF TTLVLVLVLA IAAGVGAIVF YNRTNLPDPN KDFQTNTSFI YFNDSKTKLG    60
SLSVQNRQTI GYEQMPKSIK EAAISAENRT FWSDQGISIG GIVRAAWTIA RGGEMQGGST   120
ITQQYIKILY LSQDRTMQRK LKELVLAVKM GKQVPKEDIL AGYLNTIYFG RGAYGIQAAA   180
KSYFNVDASK LTVPQSAVLA SILNNPTLFD PSGGAKARER LLNRYRYVLD GMLEAGNITQ   240
AEHDEYSRKL PAFPEVPINN RWGGTNGYLL KMVQNELLDD GFTDSQINGG GLKVTTTFDP   300
AAQKAAVATG QKYKKLAGSN AGKNGAKNLH PAIASVKVGT GEVLALYGGD DYITSTRSWA   360
```

-continued

```
LQARPAASTF KTYAVIAGMR NGFSLKSKLN GDTFTPQGDS VPIRNEFSEQ YGDVTLQKAT   420
EDSINTAFVD MMTQIDNGPQ AMLKAANDAG VPKGSGWDLN NRMPLGVAEV SPLDQATGYA   480
TIANEGKYVP SHVVAKVTDS SGKTLYTAKT TGKQTIQKDI AHDTTYALEN VVNEGTGSAV   540
SNLGYPVAGK TGTNGVKDDI TSAWFVAYTR QISTAVMYVA GDGGNEDLDP YAAEGDSTFF   600
GGTYPARTWA SYMKVAMKGL PSQDFPKPDK VNLSGKHYGN TQRETLRTPT PTPTPTPSET   660
RTPTPEPTQS STPSRPEPTQ TSSEPEPTDT PSQPEPTDTP SRPLPSLPKP TLPGIPGPSD   720
GDDGDNGATG R                                                       731
```

METHODS FOR ORGANIC ACID PRODUCTION

CLAIM OF PRIORITY

This application is a divisional application of and claims priority under 35 U.S. C. § 120 to U.S. application Ser. No. 17/073,977, filed on Oct. 19, 2020, which is a continuation application of and claims priority under 35 U.S.C. § 120 to U.S. application Ser. No. 16/443,554, filed on Jun. 17, 2019, now U.S. Pat. No. 10,808,266, which in turn claims the benefit under 35 USC § 119(e) to U.S. Patent Application Ser. No. 62/686,463, filed on Jun. 18, 2018, the entire contents of each of which are incorporated herein by reference.

SEQUENCE LISTING

This application contains a Sequence Listing that has been submitted electronically as an XML file named 37942-0022003.xml. The XML file, created on Apr. 25, 2023, is 37,376 bytes in size. The material in the XML file is hereby incorporated by reference in its entirety.

TECHNICAL FIELD

The disclosure generally relates to microbial cell lines that overproduce organic acid and methods of making the same.

BACKGROUND

Organic acids refer to carbon-containing compounds having acidic properties. Examples of organic acids include acetic acid, citric acid, gluconic acid, lactic acid, propionic acid, among many others. Because they are fully degradable, organic acids can be used in the production of biodegradable polymers. They also have other important industrial applications, including as food additives.

SUMMARY

The disclosure provides microbial cell lines suitable for industrial-scale production of organic acids and methods of making and isolating such cell lines.

In one aspect, a method of making and isolating a microbial cell line is provided, where the isolated microbial cell line overproduces an organic acid compared to the parental microbial cell line. The method uses serial passage of a parental strain in pH-controlled culture media supplemented with the organic acid, preferably in non-immobilized culture, where the pH is controlled at a value above the pKa value of the organic acid. In some embodiments, the pH is preferably in the range between about 5.5 and about 7.5, more preferably at or near neutral, between about 6.0 and about 7.0, and most preferably at about 7.0. In some embodiments, the culture media is solidified. In some embodiments, the culture medium is supplemented with the organic acid in an amount sufficient to inhibit normal microbial cell growth, e.g., to reduce doubling rate or growth rate, e.g., by at least 5%, 10%, 20%, 30%, 40%, 50%, or more. In some embodiments, the organic acid is supplemented at a progressively increasing amount in successive iterations of the serial passage. In some embodiments, the organic acid is supplemented at the same amount in successive iterations of the serial passage. In some embodiments, the organic acid is propionic acid, lactic acid, acetic acid, or butyric acid. In some embodiments, the organic acid is propionic acid, e.g., the culture media is supplemented with about 1.0%-3.0% of propionic acid, e.g., about 3.0% of propionic acid. In some embodiments, the parental cell line is a wild-type organism. In some embodiments, the parental cell line is a microbial cell line is derived from unicellular microbes.

In another aspect, a microbial cell line that overproduces an organic acid is provided, where the microbial cell line is made and isolated using serial passage in pH-controlled culture media supplemented with the organic acid, where the pH is controlled at a value above the pKa value of the organic acid, preferably in the range between about 5.5 and about 7.5, more preferably at or near neutral, between about 6.0 and about 7.0, and most preferably at about 7.0.

In another aspect, a microbial cell line that overproduces an organic acid is provided, where the microbial cell line has mutations that primarily alter, directly or indirectly, the structure, composition, and/or function of the cellular envelope. Preferably, the microbial cell line includes at least 2 genome mutations identified in Table 3 or analogous mutations. More preferably, the microbial cell line includes all of the genome mutations identified in Table 3 or homologous mutations. In one embodiment, the microbial cell line includes mutations in at least 2 genes identified in Table 3 or analogous mutations thereto. In another embodiment, the microbial cell line includes mutations in all of the genes identified in Table 3 or their homologs (e.g., homologous genes in another species described herein). In another embodiment, the microbial cell line includes a mutation in O-antigen ligase domain-containing protein. In another embodiment, the microbial cell line includes a mutation in M18 family aminopeptidase. In another embodiment, the microbial cell line includes a mutation in amino acid permease. In another embodiment, the microbial cell line includes a mutation in adenine glycosylase.

The microbe can be any microbe that produces an organic acid. In one embodiment, the microbe is from the genus *Propionibacterium* (*Acidipropionibacterium*), and more preferably the species *P. acidipropionici*. In another embodiment, the microbe is from the genus *Lactobacillus*, and more preferably the species *L. acidophilus*. In another embodiment, the microbe is from the genus *Acetobacter*. In another embodiment, the microbe is from the genus *Gluconobacter*. In another embodiment, the microbe is from the genus *Clostridium*, and more preferably the species *C. butyricum*. In some embodiments, the organic acid is propionic acid. In some embodiments, the organic acid is lactic acid. In some embodiments, the organic acid is acetic acid. In some embodiments, the organic acid is butyric acid.

Also provided herein are methods of producing organic acids using the methods and microbes described herein.

DETAILED DESCRIPTION

Figure 1:
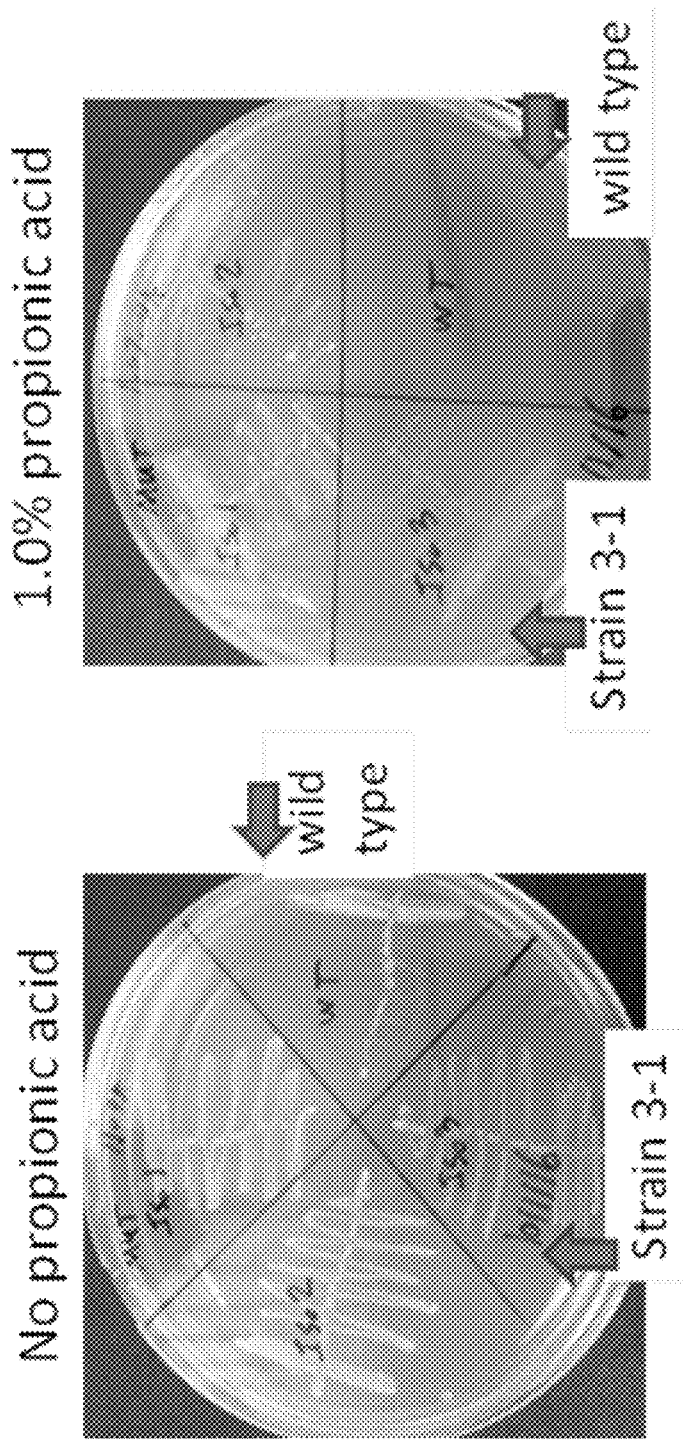
FIG. 1 shows growth of wild-type and mutant *P. acidipropionici* on solid buffered medium with or without addition of 1.0% PA, showing the phenotype of Strain 3-1.

The most common organic acids are carboxylic acids, whose acidity is associated with the carboxyl group (—COOH). They are generally weak acids with pKa values between about 4-5. Propionic acid ("PA"), for example, is a carboxylic acid with the chemical formula $C_2H_5COOH$ or $C_3H_6O_2$. It is a colorless, oily, and pungent (think Swiss cheese and sweat) liquid and has physical properties between those of the smaller carboxylic, formic, and acetic acids, and the larger fatty acids. It has a molecular weight of about 74.1 g/mol, and a pKa of about 4.9, which means in a solution having a pH of about 4.9, half of the PA is in the protonated (or undissociated), uncharged state ($C_2H_5COOH$), while the other half is in the deprotonated (or dissociated), negatively charged state ($C_2H_5COO^-$), known as propionate or propanoate ion, which can form salt or ester compounds. As the pH decreases (becoming more acidic), more PA is in the protonated, uncharged state; when the pH increases (becoming more basic), more PA is in the deprotonated, negatively charged state.

Because PA inhibits the growth of mold and some bacteria at levels between 0.1 and 1% (w/v), PA and its salts are used as a preservative in both animal feed and human food (such as baked goods). In the United States, PA is "generally recognized as safe," or GRAS, by the Food and Drug Administration when used as a food additive. It is also approved for use as a food additive in Australia, New Zealand, and the EU. In addition, PA is an important intermediate in the synthesis of other chemicals, such as cellulose-derived plastics, pesticides, fruit flavors, perfume bases, and pharmaceuticals.

While they are widely distributed in nature, commercial production of organic acids has generally relied on chemical synthesis because it is more economically competitive. For example, PA is currently commercially produced almost exclusively through petrochemical processes. As prices for crude oil and petrochemicals increase, along with the rapid development in the biotechnology field, the economic gap between manufacturing costs of PA via chemical synthesis and via microbial fermentation is narrowing. Coupled with growing concerns about energy shortages and environmental pollution, there has been an increasing interest in commercial-scale biosynthesis of organic acids such as PA from renewable resources.

Microbial production of organic acids by fermentation has been known and used for centuries. For example, *Aspergillus niger* and *Yarrowia lipolytica* have been used to produce citric acid; *Lactobacillus* has been used to produce lactic acid; *Clostridium* has been used to produce acetic acid; *Aspergillus niger* and *Gluconobacter* have been used to produce gluconic acid.

*Propionibacterium* is the microorganism most often used in the production of PA (as well as vitamin B12 and Swiss cheese). *Propionibacterium* is a gram-positive, non-motile, non-spore forming, rod-shaped, anaerobic genus of bacteria that includes the species *P. freudenreichii, P. acidifaciens, P. cyclohexanicum, P. australiense, P. acidipropionici, P. jensenii, P. thoenii, P. microaerophilum, P. olivae, P. damnosum, P. propionicum, P. acnes, P. avidum, P. granulosum, P. humerusii*, and *P. lymphophilum*. For industrial PA production, the most commonly used strain is *P. acidipropionici*. (A proposal has been made to reclassify the species within the genus *Propionibacterium* into three novel genera: *Acidipropionibacterium, Cutibacterium*, and *Pseudopropionibacterium* (Scholz & Kilian 2016). However, *Propionibacterium acidipropionici* and *Acidipropionibacterium acidipropionici* are still used somewhat interchangeably.) The optimal pH and temperature for *Propionibacterium* cell growth are about 6.0-7.0 and about 30-37° C., respectively (Ahmadi et al. 2017). Cell growth is inhibited in pH less than about 5.0, although fermenters started at neutral pH can reach pH 4.4 (Rehberger and Glatz 1998). Ahmadi et al. provides an overview of PA production on several carbon sources by various species of *Propionibacterium* as reported in the literature (Ahmadi et al. 2017) and is incorporated herein by reference.

PA can also be produced by other anaerobic bacteria, such as certain species of *Anaerovibrio, Bacteroides, Clostridium, Fusobacterium, Megasphaera, Propionispira, Selenomonas*, and *Veillonella*.

There are a number of fermentation pathways that convert carbon sources to PA through a series of enzymatic reactions. The primary fermentation pathway involved in PA production, especially in propionibacteria, is known as the Wood-Werkman cycle, which produces propionate from pyruvate, the terminal product from glycolysis, and involves many intermediates, including oxaloacetate, malate, fumarate, succinate, succinyl-CoA, methylmalonyl-CoA, and propionyl-CoA, and many enzymes, including oxaloacetate transcarboxylase, biotin-dependent carboxytransferase, CoA transferase, fumarate hydrolase, lactate dehydrogenase, coenzyme $B_{12}$-dependent methylmalonyl-CoA mutase, malate dehydrogenase, and succinate dehydrogenase.

While most pyruvate is converted to PA/propionate during fermentation, some is converted to acetate. The acetate formation pathway involves intermediates acetyl CoA and acetyl phosphate, and enzymes pyruvate dehydrogenase complex, phosphotransacetylase, and acetate kinase.

A number of carbon sources have been used for microbial PA production, including glucose, fructose, maltose, sucrose, xylose, lactose, glycerol, lactate, flour hydrolysate, molasses, whey, and a combination thereof. A number of culture systems such as batch, fed-batch, and continuous fermentation have been used.

However, for commercial-scale microbial production of organic acids to be economically viable, the fermentation process must be able to convert carbon sources at a high yield (amount of organic acid production from carbon source, typically measured in g/g) and high productivity (rate of organic acid production, typically measured in g/L·h).

Various fermentation technologies, including fed-batch, continuous culture, multi-stage, cell immobilization, and extractive fermentation systems, have been explored to increase the yield of organic acid production. However, the modest increase in yield and productivity often comes is offset by a significant increase in production cost.

For example, coculture methods have been used to produce PA using whey as feedstock (WO 85/04901; EP 0141642 A1). WO 85/04901 describes the use of *Lactobacillus casei* subspecies *rhamnosus* in the presence of *Veillonella cricetid* to interconvert lactate to propionate via a two-stage fermentation process. In the first stage, carbohydrates are converted to lactic acid by *L. casei*; in the second stage, lactic acid is fermented to PA by *V. cricetid*. (The genera *Lactobacillus* and *Veillonella* both belong to the phylum Firmicutes, whereas the genus *Propionibacterium* belongs to the phylum Actinobacteria.) EP 0141642 also describes the use of a mixed culture of lactic acid-producing bacteria (*L. casei*) and PA-producing bacteria (*P. shermanii*) to maximize the fermentation yield. The coculture systems of WO 85/04901 and EP 0141642 are reported to be very productive in terms of PA production from lactose, with final yields ranging from 20-100 g/L. However, such coculture systems have considerable implications for process parameters. For example, they suffer from a lack of control over the growth and metabolic activity of each member of the system, which can lead to failure of either member to grow or to contribute to formation of the desired product. A lack of reproducibility is common with coculture systems.

One major problem associated with microbial production of organic acids is the strong inhibitory effect of the end product on cell growth and the fermentation process, leading to low production yield and productivity. Acid tolerance was assumed to be crucial to improving the yield and productivity of PA-producing strains (Rehberger and Glatz 1998). The elevated inhibitory effect of PA at pH 4.5-5.0 as compared to lactic acid was attributed to the fact that at this pH range, about half of PA (which has a pKa of about 4.9) would be present in the undissociated, protonated, and uncharged form, whereas lactic acid (which has a pKa of about 3.1) would mostly be in the dissociated, deprotonated, and charged form. It was assumed that because the undissociated acid could penetrate the cell wall and membrane more easily, more PA than lactic acid could get into the cell and exert its inhibitory effect. Enhancement of acid tolerance was thus thought to be an effective strategy to alleviate end-product inhibition and improve PA production. Accordingly, attempts have been made to create "acid tolerant" mutants of propionibacteria under high PA and either uncontrolled or low pH conditions.

For example, adaptive evolution via serial passage has been used to obtain mutant P. acidipropionici with improved acid tolerance (Woskow and Glatz 1991; Zhu et al. 2010). Serial passage is a method of growing microorganisms such as bacteria in two or more iterations in artificial environments, often created in a laboratory setting, to generate spontaneous mutations in the microorganisms as they evolve over the course of the experiment to adapt to one or more new environmental conditions designed for the experiment. For example, repeatedly subjecting microbes to extreme acidic conditions will lead to spontaneous mutations that allow the microbes to adapt to or tolerate such conditions.

In prior work, to create mutations that confer acid-tolerance, the mutant P. acidipropionici strains were adapted to increasing PA concentrations by repeated and serial transfers in selection media containing increasing amounts of PA (from 0.5% to 5% (Woskow and Glatz 1991) or 1.5 g/L to 20 g/L (Zhu et al. 2010)) over a period of one year or longer. Importantly, in these experiments, pH in the selection media having increasing amounts of PA was not controlled, presumably because it was assumed that the inhibitory effects on cell growth and PA production were caused by the acidity of PA.

P. acidipropionici mutant(s) with enhanced PA production has also been obtained by immobilization and adaptation in a fibrous-bed bioreactor (Suwannakham and Yang 2005; Suwannakham 2005). The ability to obtain acid-tolerant mutant(s) in fibrous-bed bioreactor was attributed to the high cell density and viability maintained in the bioreactor and distinct physiology and survivability of immobilized cells as a result of their direct contact with each other and with a solid surface. The higher PA production was attributed in part to higher activity levels of oxaloacetate transcarboxylase and CoA transferase in the mutant(s). Despite the higher PA yield, in the fibrous-bed bioreactor with high cell density, cell growth is limited. Moreover, fibrous-bed bioreactors are expensive and not scalable, and their uses are limited to small-to-medium scale productions.

More recently, random mutagenesis strategies such as genome shuffling have been used to accelerate directed microbial evolution. For example, Guan et al. reported the use of genome shuffling to generate an acid-tolerant mutant P. acidipropionici strain (Guan et al. 2012). To obtain the strain, four successive rounds of genome shuffling via protoplast fusion were performed, and the acid-tolerant strain was selected using media supplemented with increasing amounts of PA (from 5 to 20 g/L). Again, pH in the selection media having increasing amounts of PA was not controlled, presumably because it was assumed that the inhibitory effects on cell growth and PA production were caused by the acidity of PA.

Subsequent analyses identified 24 proteins that significantly differed between the parental and shuffled strains (Guan et al. 2014). The detected proteins were reported to fall into four broad functional classes: cellular metabolism and energy production; DNA replication, RNA synthesis, and translation; posttranslational modification, protein folding, and chaperones; and hypothetical proteins of unknown function.

In another study, genome shuffling was used to generate acid-tolerant mutant P. acidipropionici, P. intermedium, and P. jensenii strains (WO 2017/055932 A2). Three successive rounds of genome shuffling were performed for each set of strains, each followed by selection of colonies from the acidic (pH 3) side of pH/PA gradient plates prepared using agar culture media supplemented with 5 g/L of PA at either pH 3 or pH 6.5. Final individual recombinants were randomly selected after serial dilutions in culture media plates and screened in a 96 well plate containing 100 μl of culture media at pH 5 and 25 g/L of PA. The mutant strains were reported to have enhanced yields of PA relative to native Propionibacterium and other known derivative strains. Genomic analyses of one of the mutant P. acidipropionici strains identified a number of modified genes, including those encoding the ABC polar amino acid transporter, the Cytochrome C biogenesis protein, the ABC multiple sugar transporter, the large subunit of ribosomal RNA, the long chain acyl-CoA synthetase, and the cation diffusion facilitator. In addition, an extra copy of the whole ribosomal RNA gene and an extra copy of the arginine deiminase regulon (ArgR) with a point mutation were found in the mutant strain.

Targeted metabolic engineering of propionibacteria has also been used to increase PA production. These studies generally target enzymes involved in pyruvate metabolism pathways to, for example, either inhibit the acetate formation pathway or enhance the PA formation pathway. For example, Yang and Suwannakham created engineered P. acidipropionici strains with genes encoding acetate kinase (which catalyzes conversion of acetyl phosphate into acetate) and/or phosphotransacetylase (which catalyzes conversion of acetyl CoA into acetyl phosphate) knocked out, with the goal of eliminating or reducing acetate formation and thereby enhancing PA production (US 2011/0151529 A1; Suwannakham 2005).

Yang et al. created engineered P. acidipropionici and P. freudenreichii subsp. shermanii strains transformed with propionyl-CoA:succinate CoA transferase genes to increase PA production by overexpression propionyl-CoA:succinate CoA transferase, which catalyzes conversion of propionyl CoA into propionate (WO 2012/064883 A2). The resulting strains were reported to have increased PA production and resistance to PA, as well as resistance to acidic pH in general. The increased CoA transferase activity is believed to increase carbon flux through the PA formation pathway over the acetate formation pathway.

The table below describes a list of genes that have been manipulated using recombinant DNA. These genes constitute conventional genetic targets where regulatory mutations might be expected to increase PA yields.

TABLE 1

| Gene(s) | Organism | Effect | Reference |
|---|---|---|---|
| OtsA (trehalose biosynthesis) | P. acidipropionici | Artificially over-expressed | Jiang et al. 2015 |
| Several genes in arginine deaminase and glutamate decarboxylase systems | P. jensenii | Artificially over-expressed | Guan et al. 2016 |
| Propionyl-CoA: succinate CoA transferase | P. acidipropionici P. shermanii | Artificially over-expressed | Wang et al. 2015 WO 2012/064883 A2 |
| Acetate kinase | P. acidipropionici | Artificial knock out | Suwannakham et al. 2006 Suwannakham 2005 US 2011/0151529 A1 |
| Phosphotransacetylase | P. acidipropionici | Artificial knock out | US 2011/0151529 A1 |

Targeted genetic engineering in propionibacteria, however, is challenging. As an initial matter, the effect of acid alteration and stress on bacterial physiology is complex and not well understood, making it difficult to improve tolerance towards organic acids through manipulation of specific genes. Indeed, despite knowledge about the identity of the intermediates and enzymes in the Wood-Werkman pathway that form PA in propionibacteria, genetic manipulations of the genes in this pathway have not increased PA yields to a significant extent.

Moreover, the high GC content in propionibacteria makes it difficult to identify the locations of individual genes and all of the coding regions in the genome, which complicates genetic manipulation. In addition, there are only a small number of cloning vectors available for introducing recombinant DNA into propionibacteria cells, which are known to have low transformation efficiency. Selection of transformants is also complicated by the ability of propionibacteria to quickly develop spontaneous resistance to antibiotic markers.

In addition to these challenges, the use of recombinant DNA for producing microbial cell lines is incompatible with the development of an organic food ingredient such as PA. At least in the United States, PA or other organic acids produced by genetically engineered microbes cannot be labeled as "organic" or "natural preservative," which is especially important in the food industry. Therefore, there remains a need for new microbial strains suitable for industrial-scale production of organic acids and methods of making and isolating such strains.

The toxicity of organic acids towards microbes is not well understood despite its relevance in the food and chemical industries that use fermentation for organic acid production. Despite knowledge about the identity of the intermediates and enzymes in the Wood-Werkman pathway that forms PA in propionibacteria, genetic manipulations of the genes in this pathway have not increased PA yields to a significant extent. One reason could be that these genes do not limit PA formation. Therefore, altering their sequence or expression would not change PA levels. Instead, it is argued here that other cellular targets control PA yields, but their identities could not be predicted based on current knowledge. The unknown process is what limits PA formation. Since this process is not known, the genes involved in this process cannot be predicted.

Prior efforts in creating PA-resistant bacteria through serial passage or genome shuffling have generally used media with increasing amounts of PA but either without pH control or at a pH significantly below the pKa of PA. This is based on the idea that toxicity, and therefore resistance, arises from the concentration of the organic acid. However, this approach does not consider the mechanism of organic acid uptake by the cell that involves the transporter system, which depends on the nature of the transporter and the membrane or envelope in which it is located.

Organic acids are weak acids with pKa values generally between about 4-5. The relationship between pH and pKa is described by the Henderson-Hasselbalch equation:

$$pH = pKa + \log_{10}([A^-]/[HA])$$

wherein [HA] is the concentration of the protonated, undissociated, and uncharged weak acid, and [A$^-$] is the concentration of the deprotonated, dissociated, and negatively charged conjugate base. In a typical fermentation process, the pH of the microbial culture when the organic acid reaches maximum concentration is approximately at the pKa of the organic acid without the use of a buffering agent. A solution having a pH of about 4-5 is not that acidic relative to the known pH tolerance of organic acid producing bacteria. Most of these bacteria do grow at pH values in this range, although the optimum pH for cell growth is typically about 6-7.

Intracellular transport of organic acids can be achieved through diffusion or through the action of membrane transport protein systems depending on whether the organic acids are charged or uncharged. When organic acids are not deprotonated or dissociated, they are uncharged. In this state, they can diffuse across the cellular membranes without reliance on transport systems. Charged molecules, however, always require a transport system to be translocated across membranes.

At a pH value that equals its pKa value, half of the organic acid is in the protonated (or undissociated), uncharged form, while the other half is in the deprotonated (or dissociated), negatively charged form. At pH values below their pKa values, organic acids would mostly be uncharged because their carboxyl groups would be protonated. At pH values above their pKa values, organic acids would mostly be unprotonated or dissociated and therefore negatively charged.

At high concentrations of the organic acid, the pH is relatively low, and the organic acid would mostly be in the uncharged state and could diffuse into the cell in its acid form. This is the basis for prior efforts to isolate organic acid resistant microbes either without pH control or at a pH significantly below the pKa of the organic acid. The approach in theory would generate cell lines with mutations that produced resistance due to diffusion-based organic acid cell entry. It was assumed that the uncharged organic acid would diffuse through the cell membrane into the cytoplasm and release protons due to the relatively alkaline pH inside the cell; the increase in intracellular acidity would inhibit cell growth and organic acid formation. In other words, it was assumed that organic acids in their uncharged state limited their own production. Despite the published literature and patents, in our experience, this approach does not generate resistant microbes effectively, and may require years of passage to work.

We hypothesized that it was not the acidity of the organic acid that was toxic, as previously assumed by others. Rather, it was the deprotonated, negatively charged form or the neutral salt of the organic acid (propionate) that was toxic, and would be more effective as a selection agent to recover spontaneous resistance mutations.

Unlike prior efforts, we hypothesized that the use of pH control at a value above the pKa value of the organic acids to be produced, and preferable at least 1 unit above, would ensure that most of the organic acids remain in a charged and deprotonated form. In this form, they would remain dependent on protein transport systems for intracellular uptake. This would avoid recovery of cell lines with mutations that produced resistance due to diffusion-based organic acid cell entry, if such mutations could be discovered.

Specifically, the process used was serial passage of the starting microbial cell line (usually but not necessarily a wild-type) in free-cell (i.e. non-immobilized or planktonic) culture in a bacteriologic culture medium supplemented with organic acid of interest in an amount that is sufficient to inhibit normal microbial growth (either in progressively increasing amounts or the same amount for all passages) under conditions of continued pH control at a specific pH that is above the pKa value of the organic acid. The pH is controlled at a value above the pKa value of the organic acid, preferably in the range between about 5.5 and about 7.5, more preferably at or near neutral, between about 6.0 and about 7.0, and most preferably at about 7.0. Although the present examples describe the use of Propionibacterium, other microbes can be used that are fermentative organisms that excrete organic acids, e.g., Lactobacillus, Acetobacter, Gluconobacter, or Clostridium. The organic acid used can be, e.g., PA, lactic acid, acetic acid, or butyric acid. In some embodiments, the microbe is from the genus Propionibacterium (Acidipropionibacterium), and more preferably the species P. acidipropionici, and the organic acid is PA. In some embodiments, the microbe is from the genus Lactobacillus, and more preferably the species L. acidophilus, and the organic acid is lactic acid. In some embodiments, the microbe is from the genus Acetobacter or the genus Gluconobacter, and the organic acid is acetic acid. In some embodiments, the microbe is from the genus Clostridium, and more preferably the species C. butyricum, and the organic acid is butyric acid.

Using our method of serial passage with pH control, we were able to create and isolate a new microbial strain having increased organic acid production compared to the parental strain in less than two weeks, much faster than using the conventional serial passage method described in Woskow and Glatz 1991, which generally takes at least one year. Our method is also much less complex and more easily scalable than other random mutagenesis methods such as genome shuffling and cell immobilization in a fibrous-bed bioreactor or targeted genetic engineering. Organic acids produced by mutant cell lines created and isolated using serial passage with pH control can be labeled as "organic" or "natural preservative," which is especially important in the food industry.

The same method of serial passage with pH control can be used to make and isolate a variety of microbes, including but not limited to propionibacteria, lactobacilli, acetic acid bacteria, and clostridia, that overproduce a number of organic acids, including but not limited to PA, lactic acid, acetic acid, and butyric acid. All charged molecules depend on transport systems and their associated membranes/envelopes for function. Alterations in these cellular components would achieve the same outcome as described here for propionate for other organic acids.

The same selection method (i.e., using bacteriologic culture medium supplemented with organic acid of interest in an amount that is sufficient to inhibit normal microbial growth under conditions of continued pH control at a pH that is above the pKa value of the organic acid) can be used in screening microbial libraries generated from genome shuffling or other random mutagenesis methods for isolates that exhibit increased organic acid tolerance and production.

Using this pH control method, we were able to target unique mechanisms for resistance that depended on transport and/or unpredictable intracellular targets including those involved in regulation and metabolism. Genome resequencing was then used to identify the critical genes through their mutational changes that caused the genetic resistance to high concentrations of organic acids.

The resulting mutations generally affected cellular envelope functions, as shown in Table 2.

TABLE 2

ENVELOPE AND ASSOCIATED CATEGORIES

ENVELOPE FUNCTIONS:
Transporters/membrane proteins (10 affected ORFS): Major facilitator superfamily proteins, amino acid permeases, hypothetical membrane protein, LemA membrane protein, intramembrane metalloprotease, AAA ATPase, sodium-proton antiporter
Gain-of-function in penicillin-binding protein and amino acid permease
Cell wall/peptidoglycan synthesis: Penicillin-binding proteins, O-antigen ligase domain-containing proteins (many mutations)
ENVELOPE MODIFYING FUNCTIONS:
Oxidation/reduction: Flavin reductase, alpha/beta hydrolase, pyruvate carboxylase, MocA oxidoreductase, porphyringen oxidase, KGD
Glycosyl transferases/hydrolases: Glycosyl transferase, glycosyl hydrolase, adenine glycosylase These mutations primarily altered the structure and composition and function of the cellular envelope, which consists of the cell wall and membrane(s), including the cytoplasmic membrane. A complete list of the mutations identified is provided in Table 3. We did not see any mutations in genes that have been targeted for metabolic engineering and manipulated using recombinant DNA as previously reported (see Table 1). Mutations in multiple genes appear to be required to produce the mutant phenotype (such as increased growth in media supplemented with organic acid and/or overproduction of organic acid compared to the starting microbial cell line). This is in direct contrast to prior knowledge where single genes were manipulated to try to change PA yields.

In accordance with the present invention, other conventional microbiology, molecular biology, recombinant DNA, and biochemical techniques may be used. Such techniques are fully explained in the literature and within the skill of the art. The invention will be further described in the following examples, which do not limit the scope of the methods and compositions of matter recited in the claims.

EXAMPLES

Example 1

Isolation of Strain 3-1

A P. acidipropionici (ATCC 25562) was grown to high cell density in 10 mL M24+2.0% glucose media. Serial dilutions of this culture ($10^0$ to 101) were then plated on solid M24+2.0% glucose media, solidified with agar, supplemented with 1.0%, 2.0%, and 3.0% (w/v) PA, all neutralized to pH 7.0 using sodium hydroxide. Cells were also plated on solid M24+2.0% glucose media with no additional PA.

After a 5-day anaerobic incubation at 30° C., colony growth at the different PA concentrations was assessed. Three colonies grew on the 3% PA plate plated with undiluted cells; no colony grew on the 3% PA plates plated with diluted cells. The three colonies were isolated and re-streaked onto no-PA, 2.0% PA, and 3.0% PA plates (all neutralized to pH 7.0 using sodium hydroxide), along with freshly grown wild-type *P. acidipropionici* cells.

After a second 5-day anaerobic incubation at 30° C., colony growth at the different PA concentrations was again assessed. All three isolates, but not wild-type, were able to grow on the 1.0% PA plate (FIG. 1). Only isolate #1 was able to grow on the 2.0% PA and 3.0% PA plates. This isolate was named strain 3-1 ("3" denotes 3.0% PA, and "1" denotes isolate #1). Isolate #1 was inoculated into 5 mL liquid M24+2.0% glucose media and grown to high cell density, and frozen permanents of these cells were made.

After the phenotype of resistance to 3.0% PA on solid media was confirmed for strain 3-1, PA production in 10 mL batch cultures and 1 L bioreactor cultures of this strain was compared to its parental *P. acidipropionici* (ATCC 25562) cells by HPLC in a broad range of media and cultivation conditions.

Strain 3-1 was deposited under the name NFS-2018 on Jul. 10, 2019, in the American Type Culture Collection (10801 University Blvd. Manassas, Virginia 20110-2209) and assigned Accession Number ATCC PTA-125895).

Example 2

PA Production by Strain 3-1 and Wild-Type *P. acidipropionici*

Wild type *P. acidipropionici* (ATCC 255562) and strain 3-1 were cultivated from a frozen permanent at 30° C. under anaerobic condition in M24 medium supplemented with 2% glucose. The cells were sub-cultured every 48 hr into fresh M24 medium starting at 10 mL then at 50 mL to use as seed for the 1 L bioreactor vessels.

For preparation of wheat flour medium, 75 g of American cake flour was added to 1 L of ddH2O in a sterile 2 L flask while mixing. One mL of Enzeco® alpha-amylase and 500 mL of 50 ppm of $CaCl_2$ was added to the mixture to hydrolyze the cake flour. The pH was adjusted to 6.0 by adding 5 mL of 5M NaOH and the temperature was held at 90° C. for 1 hour. The mixture was allowed to cool then incubated at 37° C. overnight. After the overnight incubation, the temperature was raised to 60° C. and pH adjusted to 7.0 by adding 2 mL of 5M NaOH. To release glucose, 1 mL of Enzeco® glucoamylase, 0.05 g of protease, 0.4 g of MgSO4, and 10 g of Ohly KAT yeast extract were added to the mixture while stirring. The mixture was held at 60° C. for 2 hours. The mixture was allowed to cool then added to a glass jacketed bioreactor vessel then sealed. Before autoclaving, the pH was calibrated.

Figure 2:
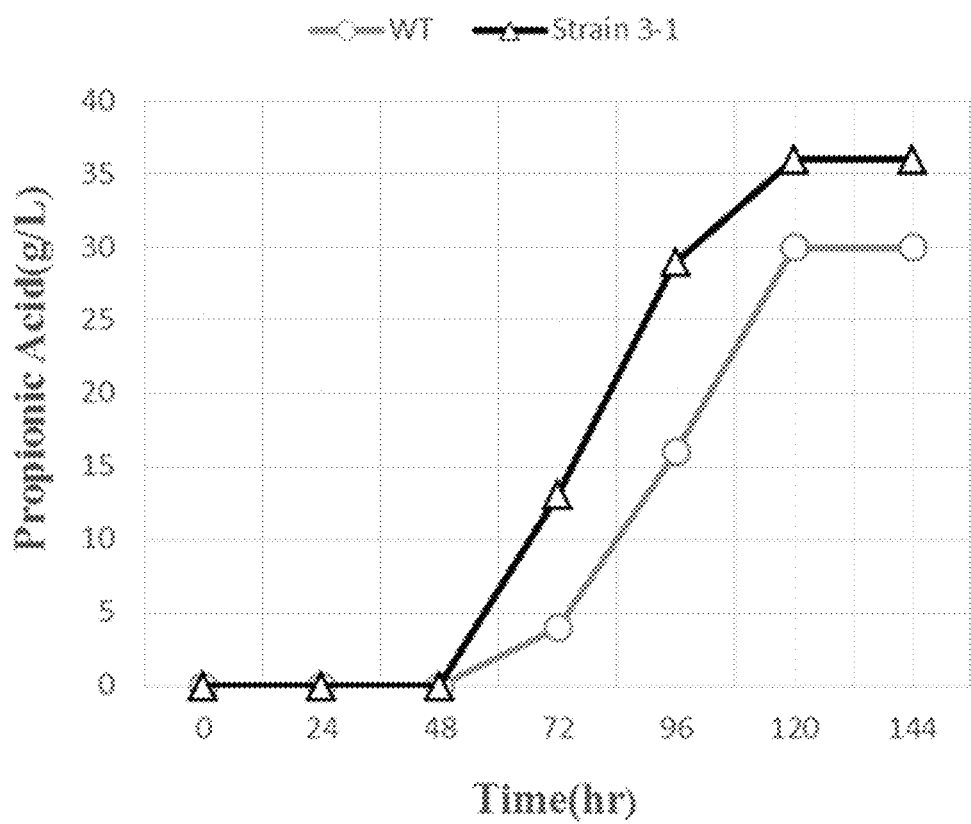
FIG. 2 shows production of PA by a mutant strain of *P. acidipropionici* (Strain 3-1) relative to wild-type in bioreactors using bleached American Beauty Cake Flour (WFM as bolus). 1:200 inoculation, 1 L working culture, 5% (w/v) glucose equivalent WFM, 30° C., pH 7 (NaOH, 5M).

Fermentations were performed at 1 L volumes in the 3 L bioreactor vessels. The temperature was maintained at 30° C., the pH was maintained at 7.0 using 5M NaOH, and cultures were agitated at 200 rpm. 3 mL of filtered sterile trace element solution was added to the bioreactor before inoculation. The glucose concentration was determined using a YSI 2900 analyzer. The 1 L of wheat flour medium was seeded with 5% inoculum. Samples were removed every 24 hours for PA analysis on the HPLC. The results are shown in FIG. 2.

Both strain 3-1 and the parental wild-type strain reached maximum PA concentration at about 120 hours. The maximum concentration of PA produced by strain 3-1 is about 36 g/L, compared to about 30 g/L by the parental wild-type strain.

Additional experiments were carried out under 5-6 different conditions, 3-4 times each, to compare PA production by strain 3-1 and wild-type *P. acidipropionici*. Results similar to those shown in FIG. 2 were obtained. There is a minimum of 15% increase in PA production by strain 3-1 compared to the wild-type after 60 hours of culturing.

Example 3

Genomic Analyses of Strain 3-1

Genome resequencing of strain 3-1 was used to identify the critical genes through their mutational changes that caused the genetic resistance to high concentrations of organic acids.

65 loss of function mutations in 29 genes were identified. The mutations generally affected cellular envelope functions, as shown in Table 2. These mutations primarily alter the structure and composition and function of the cellular envelope, which consists of the cell wall and membrane(s), including the cytoplasmic membrane. A complete list of the mutations identified in strain 3-1 is provided in Table 3.

TABLE 3

STRAIN 3-1 GENOME MUTATIONS

| Coordinates | ORF | SEQ ID NO. | Change |
|---|---|---|---|
| Non-synonymous | | | |
| 130744-130746 | ASQ49_RS00690 class I SAM-dependent methyltransferase | 1 | Arg → His |
| 130744-130746 | ASQ49_RS00695 MFS transporter | 2 | Thr → Pro |
| 130748 | ASQ49_RS00690 class I SAM-dependent methyltransferase | 1 | Pro → Leu |
| 130752 | ASQ49_RS00695 MFS transporter | 2 | Arg → Gly |
| 181601 (80% confidence) | ASQ49_RS00915 LemA family protein | 3 | Insertion (no frameshift) |
| 181607-181609 | ASQ49_RS00915 LemA family protein | 3 | Gln → Leu |
| 240311 | ASQ49_01155 Flavin reductase | 4 | Pro → His |
| 240440 | ASQ49_01155 Flavin reductase | 4 | Ala → Val |
| 281222 | ASQ49_RS01330 Hypothetical protein (BLAST hit to MFS transporter) | 5 | Trp → STOP |
| 344598 | ASQ49_RS01635 MFS transporter | 6 | Thr → Pro |
| 525954 | ASQ49_RS02385 glycosyl transferase family 1 | 7 | Ala → Glu |
| 548143-548147 | ASQ49_RS02475 Hypothetical protein (Strong BLAST hits to O-antigen ligase and membrane protein) | 8 | Ala → Gly Gly → Leu |
| 548153-548156 | ASQ49_RS02475 Hypothetical protein (Strong BLAST hits to O-antigen ligase and membrane protein) | 8 | Ala → Val Gly → Leu |
| 548162 | ASQ49_RS02475 Hypothetical protein (Strong BLAST hits to O-antigen ligase and membrane protein) | 8 | Ala → Val |
| 558158-558160 | ASQ49_RS02520 O-antigen ligase domain-containing protein | 9 | His → Gly |
| 558181 | ASQ49_RS02520 O-antigen ligase domain-containing protein | 9 | Gln → His |
| 558228 | ASQ49_RS02520 O-antigen ligase domain-containing protein | 9 | Ala → Thr |

TABLE 3-continued

STRAIN 3-1 GENOME MUTATIONS

| Coordinates | ORF | SEQ ID NO. | Change |
|---|---|---|---|
| 558252 | ASQ49_RS02520 O-antigen ligase domain-containing protein | 9 | Ser → Pro |
| 558258 | ASQ49_RS02520 O-antigen ligase domain-containing protein | 9 | Ser → Pro |
| 558266 | ASQ49_RS02520 O-antigen ligase domain-containing protein | 9 | Arg → Leu |
| 558273 | ASQ49_RS02520 O-antigen ligase domain-containing protein | 9 | Ser → Ala |
| 558279 | ASQ49_RS02520 O-antigen ligase domain-containing protein | 9 | Gln → Glu |
| 558282 | ASQ49_RS02520 O-antigen ligase domain-containing protein | 9 | Glu → Gln |
| 558288-588290 | ASQ49_RS02520 O-antigen ligase domain-containing protein | 9 | Leu → Pro |
| 558291-558293 | ASQ49_RS02520 O-antigen ligase domain-containing protein | 9 | Glu → Val |
| 558306 | ASQ49_RS02520 O-antigen ligase domain-containing protein | 9 | Pro → Ala |
| 558308-558310 | ASQ49_RS02520 O-antigen ligase domain-containing protein | 9 | Thr → Ser |
| 562835 | ASQ49_RS02535 O-antigen ligase domain-containing protein | 10 | Val → Leu |
| 562840 | ASQ49_RS02535 O-antigen ligase domain-containing protein | 10 | Ala → Val |
| 562843 | ASQ49_RS02535 O-antigen ligase domain-containing protein | 10 | Gly → Ala |
| 566353 (*50% frequency) | ASQ49_RS02550 penicillin-binding protein | 11 | Lys → Gln |
| 566356 (*50% frequency) | ASQ49_RS02550 penicillin-binding protein | 11 | Ala → Ser |
| 618017-618019 | ASQ49_RS02820 Phosphotransferase | 12 | Glu → Ala |
| 738302 | ASQ49_RS03340 Alpha/beta hydrolase | 13 | Thr → Ala |
| 742073 | ASQ49_RS03360 Hypothetical protein (BLAST hits to intramembrane metalloprotease) | 14 | Ile → Leu |
| 1176596 | ASQ49_RS05220 gfo/Idh/MocA family oxidoreductase | 15 | Ala → Val |
| 1279986 | ASQ49_RS05630 Alpha/beta hydrolase | 16 | Ile → Val |
| 1331356 | ASQ49_RS05840 Amino acid permease | 17 | Gly → Ser |
| 1331366 | ASQ49_RS05840 Amino acid permease | 17 | Arg → His |
| 1521847 | ASQ49_RS06625 Hypothetical protein (BLAST hits to protoporphyrinogen oxidase) | 18 | Thr → Ala |
| 1816621 | ASQ49_RS07985 Adenine glycosylase | 19 | Ser → Ala |
| 1816687 | ASQ49_RS07985 Adenine glycosylase | 19 | In-frame insertion (1 amino acid) |
| 1817191 | ASQ49_RS07985 Adenine glycosylase | 19 | Gly → Glu |
| 1817202 | ASQ49_RS07985 Adenine glycosylase | 19 | Glu → Ala |
| 1854503 | SQ49_RS08150 Hypothetical protein (BLAST hit to sodium-proton antiporter) | 20 | Lys → Arg |
| 1854520 | SQ49_RS08150 Hypothetical protein (BLAST hit to sodium-proton antiporter) | 20 | Ile → Met |
| 2679601 | ASQ49_12020 multifunctional oxoglutarate decarboxylase/oxoglutarate dehydrogenase thiamine pyrophosphate-binding subunit/dihydrolipoyllysine-residue succinyltransferase subunit (kgd) | 21 | His → Asp |
| 2927020 | ASQ49_RS13125 Amino acid permease | 22 | In-frame insertion (4 amino acids) |
| 2927030 | ASQ49_RS13125 Amino acid permease | 22 | Gly-Ser → Ala-Ala |
| 2928883 | ASQ49_RS13130 Hypothetical protein (glycosyl gydrolase family) | 23 | Asn → Tyr |
| 3517645 (*50% frequency) | ASQ49_RS15965 M18 family aminopeptidase | 24 | Thr → Arg |
| 3517646 (*50% frequency) | ASQ49_RS15965 M18 family aminopeptidase | 24 | Thr → Ser |
| 3517648 (*50% frequency) | ASQ49_RS15965 M18 family aminopeptidase | 24 | Ser → Thr |
| 3517649 (*50% frequency) | ASQ49_RS15965 M18 family aminopeptidase | 24 | Ser → Gly |
| 3517652 | ASQ49_RS15965 M18 family aminopeptidase | 24 | Ser → Tyr |
| 3517655 | ASQ49_RS15965 M18 family aminopeptidase | 24 | Ser → Asn |
| FRAMESHIFTS | | | |
| 558244 | ASQ49_RS02520 O-antigen ligase domain-containing protein | 9 | |
| 558246 | ASQ49_RS02520 O-antigen ligase domain-containing protein | 9 | |
| 2867178 | ASQ49_RS12835 AAA ATPase | 25 | |
| FRAMESHIFT REPAIRS | | | |
| 448285 | ASQ49_RS02075 DUF1116 domain-containing protein | 26 | |
| 561527 | ASQ49_RS02530 Glycosyl transferase | 27 | |
| 900222 | ASQ49_RS03980 acetyl-CoA carboxylase biotin carboxyl carrier protein subunit | 28 | |
| 919056 | ASQ49_RS04070 Penicillin-binding protein | 29 | |
| 1330401 | ASQ49_RS05840 Amino acid permease | 17 | |
| 1330407 | ASQ49_RS05840 Amino acid permease | 17 | |

Mutations in these genes (or their homologues in other species described herein) likely confer genetic resistance to high concentrations of organic acids by altering the membrane transport protein systems and/or previously unknown intracellular targets involved in regulation and/or metabolism.

Multiple mutations in the same gene imply that the gene is very important for the trait and required multiple changes to contribute to the trait. Noticeably, several genes had three or more mutations, which may indicate their critical roles in limiting organic acid formation. They include genes encoding: O-antigen ligase domain-containing protein (15 mutations in ASQ49_RS02520; 3 mutations in ASQ49_RS02535; and 3 mutations in ASQ49_RS02475 (hypothetical protein with strong BLAST hits to O-antigen ligase and membrane protein)); M18 family aminopeptidase (6 mutations in ASQ49_RS15965); amino acid permease (4 mutations in ASQ49_RS05840); and adenine glycosylase (4 mutations in ASQ49_RS07985).

REFERENCES

1. Woskow S. A., B. A. Glatz. 1991. Propionic acid production by a propionic acid-tolerant strain of *Propionibacterium acidipropionici* in batch and semicontinuous fermentation. Applied and Environmental Microbiology 57:2821-2828.
2. Zhu Y., J. Li, M. Tan, L. Liu, L. Jiang, J. Sun, P. Lee, G. Du, J. Chen. 2010. Optimization and scale-up of propionic acid production by propionic acid-tolerant *Propionibacterium acidipropionici* with glycerol as the carbon source. Bioresource Technology 101:8902-8906.
3. Wang Z., S.-T. Yang. 2013. Propionic acid production in glycerol/glucose co-fermentation by *Propionibacterium freudenreichii* subsp. *shermanii*. Bioresource Technology 137:116-123.
4. Zhuge X., L. Liu, H.-d. Shin, J. Li, G. Du, J. Chen. 2014. Improved propionic acid production from glycerol with metabolically engineered *Propionibacterium jensenii* by integrating fed-batch culture with a pH-shift control strategy. Bioresource Technology 152:519-525.
5. Zhuge X., J. Li, H.-d. Shin, L. Liu, G. Du, J. Chen. 2015. Improved propionic acid production with metabolically engineered *Propionibacterium jensenii* by an oxidoreduction potential-shift control strategy. Bioresource Technology 175:606-612.
6. Coral J. 2008. Propionic acid production by *Propionibacterium* sp. using low-cost carbon sources in submerged fermentation. Dissertation. Federal University of Parana.
7. Zhang A., J. Sun, Z. Wang, S.-T. Yang, H. Zhou. 2015. Effects of carbon dioxide on cell growth and propionic acid production from glycerol and glucose by *Propionibacterium acidipropionici*. Bioresource Technology 175:374-381.
8. Wang Z., M. Lin, L. Wang, E. M. Ammar, S.-T. Yang. 2015. Metabolic engineering of *Propionibacterium freudenreichii* subsp. *shermanii* for enhanced propionic acid fermentation: Effects of overexpressing three biotin-dependent carboxylases. Process Biochemistry 50:194-204.
9. Suwannakham S., Y. Huang, S.-T. Yang. 2006. Construction and characterization of ack knock-out mutants of *Propionibacterium acidipropionici* for enhanced propionic acid fermentation. Biotechnology and Bioengineering 94:383-95.
10. Suwannakham S., S.-T. Yang. 2005. Enhanced propionic acid fermentation by *Propionibacterium acidipropionici* mutant obtained by adaptation in a fibrous-bed bioreactor. Biotechnology and Bioengineering 91:325-337.
11. Suwannakham S. 2005. Metabolic engineering for enhanced propionic acid fermentation by *Propionibacterium acidipropionici*. Dissertation. Ohio State University.
12. Tufvesson P., A. Ekman, R. R. R. Sardari, K. Engdahl, L. Tufvesson. 2013. Economic and environmental assessment of propionic acid production by fermentation using different renewable raw materials. Bioresource Technology 149:556-564.
13. Thierry A., S.-M. Deutsch, H. Falentin, M. Dalmasso, F. J. Cousin, G. January 2011. New insights into physiology and metabolism of *Propionibacterium freudenreichii*. International Journal of Food Microbiology 149:19-27.
14. Scholz C. F. P., M. Kilian. 2016. The natural history of cutaneous propionibacteria, and reclassification of selected species within the genus *Propionibacterium* to the proposed novel genera *Acidipropionibacterium* gen. nov., *Cutibacterium* gen. nov. and *Pseudopropionibacterium* gen. nov. International Journal of Systematic and Evolutionary Microbiology 66:4422-4432.
15. Rehberger J. L., B. A. Glatz. 1998. Response of cultures of *Propionibacterium* to acid and low pH: tolerance and inhibition. Journal of Food Production 61:211-216.
16. Ahmadi N., K. Khosravi-Darani, A. M. Mortazavian. 2017. An overview of biotechnological production of propionic acid: From upstream to downstream processes. Electronic Journal of Biotechnology 28:67-75.
17. Guan N., L. Liu, X. Zhug, Q. Xu, J. Li, G. Du, J. Chen. 2012. Genome-shuffling improves acid tolerance of *Propionibacterium acidipropionici* and propionic acid production. Advances in Chemistry Research 15:143-152.
18. Guan N., H. Shin, R. R. Chen, J. Li, L. Liu, G. Du, J. Chen. 2014. Understanding of how *Propionibacterium acidipropionici* respond to propionic acid stress at the level of proteomics. Scientific Reports 4:6951.
19. Guan N., H. D. Shin, G. Du, J. Chen, L. Liu. 2016. Metabolic engineering of acid resistance elements to improve acid resistance and propionic acid production of *Propionibacterium jensenii*. Biotechnology and Bioengineering 113:1294-304.
20. Jiang L., H. Cui, L. Zhu, Y. Hu, X. Xu, S. Li, H. Huang. 2015. Enhanced propionic acid production from whey lactose with immobilized *Propionibacterium acidipropionici* and the role of trehalose synthesis in acid tolerance. Green Chemistry 15:250-259.
21. EP 0141642
22. WO 85/04901
23. US 2011/0151529 A1
24. WO 2012/064883 A2
25. WO 2017/055932 A2

The invention claimed is:

1. A method of producing an organic acid selected from propionic acid, lactic acid, acetic acid, butyric acid, or combinations thereof, the method comprising: providing a *Propionibacterium acidipropionici* cell comprising at least one loss of function mutation in a gene encoding a protein selected from the group consisting of O-antigen ligase domain-containing protein comprising the amino acid sequence of SEQ ID NO:9, amino acid permease comprising the amino acid sequence of SEQ ID NO: 17, DUF 1116 domain-containing protein comprising the amino acid sequence of SEQ ID NO:26, M18 family aminopeptidase comprising the amino acid sequence of SEQ ID NO:24, and adenine glycosylase comprising the amino acid sequence of SEQ ID NO: 19; and culturing the P. acidipropionici cell in a culture medium.

2. The method of claim 1, wherein the culture medium is maintained at a pH of from about 5.5-7.5.

3. The method of claim 1, wherein the culture medium is maintained at a pH of from about 6.0-7.0.

4. The method of claim 1, wherein said culturing is carried out at about 30° C. for about 60 to about 120 hours.

5. The method of claim 1, wherein the *P. acidipropionici* cell comprises a loss of function mutation in the gene encoding 0-antigen ligase domain-containing protein comprising the amino acis sequence of SEQ ID NO: 9..

6. The method of claim 1, wherein the organic acid is propionic acid.

7. The method of claim 1, wherein the amount of organic acid produced by the method after 60 hours of culturing is at least 15% higher as compared to the amount of organic acid produced under the same conditions using wild-type *P. acidipropionici*.

8. The method of claim 1, wherein the *P. acidipropionici* cell further comprises one or more additional mutations in a gene encoding a protein selected from the group consisting of class I SAM-dependent methyltransferase comprising the amino acid sequence of SEQ ID NO: 1, MFS transporter comprising the amino acid sequence of SEQ ID NO: 2, LemA family protein comprising the amino acid sequence of SEQ ID NO: 3, Flavin reductase comprising the amino acid sequence of SEQ ID NO: 4, comprising the amino acid sequence of SEQ ID NO: 5, MFS transporter comprising the amino acid sequence of SEQ ID NO: 6, glycosyl transferase family 1 comprising the amino acid sequence of SEQ ID NO: 7, protein comprising the amino acid sequence of SEQ ID NO: 8, O-antigen ligase domain- containing protein comprising the amino acid sequence of SEQ ID NO: 10, penicillin-binding protein comprising the amino acid sequence of SEQ ID NO: 11, phosphotransferase comprising the amino acid sequence of SEQ ID NO: 12, alpha/beta hydrolase comprising the amino acid sequence of SEQ ID NO: 13, protein comprising the amino acid sequence of SEQ ID NO: 14, gfo/Idh/MocA family oxidoreductase comprising the amino acid sequence of SEQ ID NO: 15, alpha/beta hydrolase comprising the amino acid sequence of SEQ ID NO: 16, protein comprising the amino acid sequence of SEQ ID NO: 18, protein comprising the amino acid sequence of SEQ ID NO: 20, multifunctional oxoglutarate decarboxylase/oxoglutarate dehydrogenase thiamine pyrophosphate-binding subunit/dihydrolipoyllysine-residue succinyltransferase subunit comprising the amino acid sequence of SEQ ID NO: 21, amino acid permease comprising the amino acid sequence of SEQ ID NO: 22, protein comprising the amino acid sequence of SEQ ID NO: 23, ATPase comprising the amino acid sequence of SEQ ID NO: 25, glycosyl transferase comprising the amino acid sequence of SEQ ID NO: 27, acetyl-Co A carboxylase biotin carboxyl carrier protein subunit comprising the amino acid sequence of SEQ ID NO: 28, and penicillin-binding protein comprising the amino acid sequence of SEQ ID NO: 29.

9. The method of claim 8, wherein the *P. acidipropionici* cell comprises loss of function mutations in the genes encoding class I SAM-dependent methyltransferase comprising the amino acid sequence of SEQ ID NO: 1, MFS transporter comprising the amino acid sequence of SEQ ID NO: 2, LemA family protein comprising the amino acid sequence of SEQ ID NO: 3, Flavin reductase comprising the amino acid sequence of SEQ ID NO: 4, protein comprising the amino acid sequence of SEQ ID NO: 5, MFS transporter comprising the amino acid sequence of SEQ ID NO: 6, glycosyl transferase family 1 comprising the amino acid sequence of SEQ ID NO: 7, protein comprising the amino acid sequence of SEQ ID NO: 8, O-antigen ligase domain-containing protein comprising the amino acid sequence of SEQ ID NO: 10, penicillin-binding protein comprising the amino acid sequence of SEQ ID NO: 11, phosphotransferase comprising the amino acid sequence of SEQ ID NO: 12, alpha/beta hydrolase comprising the amino acid sequence of SEQ ID NO:13, protein comprising the amino acid sequence of SEQ ID NO:14, gfo/Idh/MocA family oxidoreductase comprising the amino acid sequence of SEQ ID NO:15, alpha/beta hydrolase comprising the amino acid sequence of SEQ ID NO:16, protein comprising the amino acid sequence of SEQ ID NO:18, protein comprising the amino acid sequence of SEQ ID NO:20, multifunctional oxoglutarate decarboxylase/oxoglutarate dehydrogenase thiamine pyrophosphate-binding subunit/dihydrolipoyllysine-residue succinyltransferase subunit comprising the amino acid sequence of SEQ ID NO:21, amino acid permease comprising the amino acid sequence of SEQ ID NO:22, protein comprising the amino acid sequence of SEQ ID NO:23, ATPase comprising the amino acid sequence of SEQ ID NO:25, glycosyl transferase comprising the amino acid sequence of SEQ ID NO:27, acetyl-CoA carboxylase biotin carboxyl carrier protein subunit comprising the amino acid sequence of SEQ ID NO:28, and Penicillin-binding protein comprising the amino acid sequence of SEQ ID NO:29.

10. The method of claim 1, wherein the *P. acidipropionici* cell is of a *P. acidipropionici* cell line deposited in the American Type Culture Collection under Accession Number ATCC PTA-125895.

11. The method of claim 1, wherein the culture medium is a solidified culture medium.

12. The method of claim 1, wherein the culture medium is a liquid culture medium.

13. The method of claim 1, wherein the culture medium is supplemented with organic acid.

14. The method of claim 1, wherein the culture medium is supplemented with 1.0%-3.0% of the organic acid.

15. The method of claim 1, wherein the culture medium comprises glucose derived from wheat flour.

16. The method of claim 1, wherein said culturing comprises serial passaging.

17. The method of claim 16, wherein the culture medium is supplemented with the organic acid.

18. The method of claim 16, wherein the culture medium is supplemented with 1.0%-3.0% of the organic acid.

19. The method of claim 16, wherein the culture medium comprises glucose derived from wheat flour.

* * * * *